US009371598B2

(12) United States Patent
Chee

(10) Patent No.: US 9,371,598 B2
(45) Date of Patent: Jun. 21, 2016

(54) SPATIALLY ENCODED BIOLOGICAL ASSAYS

(75) Inventor: Mark S. Chee, Encinitas, CA (US)

(73) Assignee: Prognosys Biosciences, Inc., San Diego, CA (US)

( * ) Notice: Subject to any disclaimer, the term of this patent is extended or adjusted under 35 U.S.C. 154(b) by 783 days.

(21) Appl. No.: 13/080,616

(22) Filed: Apr. 5, 2011

(65) Prior Publication Data

US 2011/0245111 A1    Oct. 6, 2011

Related U.S. Application Data

(60) Provisional application No. 61/321,124, filed on Apr. 5, 2010.

(51) Int. Cl.
*C12Q 1/68* (2006.01)
*G01N 33/53* (2006.01)
*C40B 60/04* (2006.01)
*C40B 30/04* (2006.01)
*G01N 33/68* (2006.01)

(52) U.S. Cl.
CPC .............. *C40B 60/04* (2013.01); *C12Q 1/6809* (2013.01); *C12Q 1/6834* (2013.01); *C12Q 1/6837* (2013.01); *C12Q 1/6841* (2013.01); *C12Q 1/6869* (2013.01); *C40B 30/04* (2013.01); *G01N 33/6845* (2013.01); *G01N 2458/10* (2013.01)

(58) Field of Classification Search
CPC .............. C12Q 1/6837; C12Q 1/6874; C12Q 2565/501; C12Q 2565/513; C12Q 2565/50; C12Q 2565/514; C12Q 2565/518; C12Q 2565/519; C12Q 2565/525; C12Q 2565/531; C12Q 2565/537; C12Q 2565/543; C12Q 2565/549; G01N 21/6452; G01N 21/8903; G01N 33/53
See application file for complete search history.

(56) References Cited

U.S. PATENT DOCUMENTS

| | | | |
|---|---|---|---|
| 5,002,882 A | 3/1991 | Lunnen et al. | |
| 5,512,439 A | 4/1996 | Hornes et al. | |
| 6,210,894 B1 | 4/2001 | Brennan | |
| 6,258,558 B1 | 7/2001 | Szostak et al. | |
| 6,261,804 B1 | 7/2001 | Szostak et al. | |
| 6,281,804 B1 | 8/2001 | Haller et al. | |
| 6,344,316 B1 | 2/2002 | Lockhart et al. | |
| 6,416,950 B1 | 7/2002 | Lohse et al. | |
| 6,485,982 B1 | 11/2002 | Charlton | |
| 6,518,018 B1 | 2/2003 | Szostak et al. | |
| 6,579,695 B1 | 6/2003 | Lambalot et al. | |
| 6,632,641 B1 | 10/2003 | Brennan et al. | |
| 6,800,453 B2 | 10/2004 | Labaer et al. | |
| 6,878,515 B1 | 4/2005 | Landegren | |
| 7,118,883 B2 | 10/2006 | Inoue et al. | |
| 7,192,735 B2 | 3/2007 | Lambalot et al. | |
| 7,229,769 B2 | 6/2007 | Kozlov et al. | |
| 7,270,950 B2 | 9/2007 | Szostak et al. | |
| 7,378,242 B2 | 5/2008 | Hurt et al. | |
| 7,393,665 B2 | 7/2008 | Brenner | |
| 7,407,757 B2 | 8/2008 | Brenner | |
| 7,537,897 B2 | 5/2009 | Brenner et al. | |
| 7,544,473 B2 | 6/2009 | Brenner | |
| 7,579,153 B2 | 8/2009 | Brenner et al. | |
| 7,635,566 B2 | 12/2009 | Brenner | |
| 7,666,612 B2 | 2/2010 | Johnsson et al. | |
| 7,674,752 B2 | 3/2010 | He et al. | |
| 7,858,321 B2 | 12/2010 | Glezer et al. | |
| 8,207,093 B2 | 6/2012 | Szostak et al. | |
| 8,337,851 B2 | 12/2012 | Aukerman et al. | |
| 8,343,500 B2 | 1/2013 | Wraith et al. | |
| 2003/0087232 A1 | 5/2003 | Christians et al. | |
| 2003/0113713 A1 | 6/2003 | Glezer et al. | |
| 2003/0138879 A1 | 7/2003 | Lambalot et al. | |
| 2003/0162216 A1 | 8/2003 | Gold et al. | |
| 2003/0224419 A1 | 12/2003 | Corcoran et al. | |
| 2003/0232382 A1 | 12/2003 | Brennan et al. | |
| 2003/0235852 A1 | 12/2003 | Roberts et al. | |
| 2005/0026188 A1 | 2/2005 | Van Kessel et al. | |
| 2005/0048580 A1 | 3/2005 | Labaer et al. | |
| 2005/0164292 A1 | 7/2005 | Faroqui et al. | |
| 2005/0255548 A1 | 11/2005 | Lipovsek et al. | |
| 2005/0260653 A1 | 11/2005 | LaBaer et al. | |
| 2006/0003394 A1 | 1/2006 | Song | |
| 2006/0046313 A1* | 3/2006 | Roth et al. ............. | 436/518 |
| 2006/0134669 A1 | 6/2006 | Casasanta, III | |
| 2006/0216721 A1 | 9/2006 | Kozlov et al. | |

(Continued)

FOREIGN PATENT DOCUMENTS

EP          1712623      10/2006
WO    WO-03/010176      2/2003

(Continued)

OTHER PUBLICATIONS

Fredriksson, et al., "Protein detection using proximity-dependent DNA ligation assays," Nature Biotech., 20:473-77 (2002).
Fredriksson, et al., "Multiplexed protein detection by proximity ligation for cancer detection," Nature Methods, 4(4):327-29 (2007).
Kozlov, et al., "A High-Complexity Multiplexed Solution-Phase Assay for Profiling Protease Activity on Microarrays," Comb. Chem. And High Throughput, 11:24-35 (2008).
Niemeyer, "The developments of semisynthetic DNA/protein conjugates," Trends Biotechnol, 20(9):395-401(2002).

(Continued)

*Primary Examiner* — James Martinell
(74) *Attorney, Agent, or Firm* — Morrison & Foerster LLP

(57) ABSTRACT

The present invention provides assays and assay systems for use in spatially encoded biological assays. The invention provides an assay system comprising an assay capable of high levels of multiplexing where reagents are provided to a biological sample in defined spatial patterns; instrumentation capable of controlled delivery of reagents according to the spatial patterns; and a decoding scheme providing a readout that is digital in nature.

46 Claims, 5 Drawing Sheets

(56) References Cited

U.S. PATENT DOCUMENTS

| | | | |
|---|---|---|---|
| 2006/0216775 | A1 | 9/2006 | Burkart et al. |
| 2006/0275799 | A1 | 12/2006 | Banerjee et al. |
| 2007/0014810 | A1 | 1/2007 | Baker et al. |
| 2007/0020625 | A1 | 1/2007 | Duchaud et al. |
| 2007/0020669 | A1 | 1/2007 | Ericsson |
| 2007/0026430 | A1 | 2/2007 | Andersen et al. |
| 2007/0172873 | A1* | 7/2007 | Brenner et al. .......... 435/6 |
| 2008/0071071 | A1 | 3/2008 | LaBaer et al. |
| 2008/0108804 | A1 | 5/2008 | Hayashizaki et al. |
| 2008/0220981 | A1 | 9/2008 | McGregor |
| 2008/0293591 | A1 | 11/2008 | Taussig et al. |
| 2008/0312103 | A1 | 12/2008 | Nemoto et al. |
| 2009/0280487 | A1 | 11/2009 | Hung et al. |
| 2009/0291854 | A1 | 11/2009 | Weisinger-Mayr et al. |
| 2010/0069263 | A1 | 3/2010 | Shendure et al. |
| 2010/0099103 | A1 | 4/2010 | Hsieh et al. |
| 2010/0113302 | A1 | 5/2010 | Williams |
| 2010/0173384 | A1 | 7/2010 | Johnsson et al. |
| 2010/0184614 | A1 | 7/2010 | Ye et al. |
| 2011/0245101 | A1 | 10/2011 | Chee et al. |
| 2012/0065081 | A1 | 3/2012 | Chee |
| 2012/0129248 | A1 | 5/2012 | Chee et al. |
| 2012/0195810 | A1 | 8/2012 | Cohen et al. |
| 2012/0258871 | A1 | 10/2012 | Kozlov et al. |
| 2012/0270748 | A1 | 10/2012 | Chee et al. |
| 2013/0096033 | A1 | 4/2013 | Routenberg |
| 2013/0109595 | A1 | 5/2013 | Routenberg |

FOREIGN PATENT DOCUMENTS

| | | |
|---|---|---|
| WO | WO-2005/026387 | 3/2005 |
| WO | WO-2007/041689 | 4/2007 |
| WO | WO-2007/060599 | 5/2007 |
| WO | WO 2007/073171 | 6/2007 |
| WO | WO-2007/076726 | 7/2007 |
| WO | WO-2007/145612 | 12/2007 |
| WO | WO-2009/032167 | 3/2009 |
| WO | WO-2010/019826 | 2/2010 |
| WO | WO-2010/127186 | 11/2010 |
| WO | WO-2011/014879 | 2/2011 |
| WO | WO-2011/071943 | 6/2011 |
| WO | WO-2011/127006 | 10/2011 |
| WO | WO-2011/127099 | 10/2011 |
| WO | WO-2012/139110 | 10/2012 |
| WO | WO-2014/210223 | 12/2014 |
| WO | WO-2014/210225 | 12/2014 |

OTHER PUBLICATIONS

Chandra, et al., "Cell-free synthesis-based protein microarrays and their applications," Proteomics ePub, 5(6):717-30 (2009).
Ramachandran et al., Next-generation high-density self-assembling functional protein arrays,: Nature Methods, 5(6):535-38 (2008).
Search Report for PCT/US2010/059327, Mar. 29, 2011.
Search Report for PCT/US2011/031308, Jun. 7, 2011.
Search Report for PCT/US2011/031163, May 23, 2011.
Office Action for U.S. Appl. No. 13/266,568, mailed Mar. 29, 2013.
Response to Office Action for U.S. Appl. No. 13/266,568, filed Aug. 29, 2013.
Office Action for U.S. Appl. No. 13/388,229, mailed Dec. 24, 2012.
International Search Report and Written Opinion for PCT/US2010/033064, mailed Jul. 30, 2010.
International Preliminary Report on Patentability Chapter I for PCT/US2010/033064, issued Nov. 1, 2011.
International Search Report and Written Opinion for PCT/US2010/044134, mailed Mar. 18, 2011.
International Preliminary Report on Patentability Chapter I for PCT/US2010/044134, issued Jan. 31, 2012.
Communication Pursuant to Art. 94(3) EPC for EP 10747097.3-1405, issued Jul. 26, 2013.
Restriction Requirement for U.S. Appl. No. 13/514,045, mailed Nov. 23, 2012.
Response to Restriction Requirement for U.S. Appl. No. 13/514,045, filed Dec. 19, 2012.
Office Action for U.S. Appl. No. 13/514,045, mailed Feb. 21, 2013.
Response to Office Action for U.S. Appl. No. 13/514,045, filed Jun. 17, 2013.
Response to Office Action for U.S. Appl. No. 13/514,045, filed Jun. 27, 2013.
Final Office Action for U.S. Appl. No. 13/514,045, mailed Oct. 18, 2013.
International Preliminary Report on Patentability Chapter I for PCT/US2010/059327, issued Jun. 12, 2012.
Patent Examination Report No. 1 for AU 2010328226, issued May 9, 2013.
Supplemental European Search Report for EP 10836568.5-1403, mailed Mar. 4, 2013.
Response to Supplemental European Search Report for EP 10836568.5-1403, filed Sep. 10, 2013.
First Examination Report for EP 10836568.5-1403, dated Oct. 1, 2013.
International Preliminary Report on Patentability Chapter I for PCT/US2011/031308, issued 9 Oct. 2012.
Patent Examination Report No. 1 for AU 2011237729, issued Jul. 9, 2013.
Rule 161/162 Communication for EP 11766613.1, dated Nov. 14, 2012.
Response to Rule 161/162 Communication for EP 11766613.1, filed May 17, 2013.
Office Action for U.S. Appl. No. 13/079,878, mailed Aug. 13, 2012.
International Preliminary Report on Patentability Chapter I for PCT/US2011/031163, issued Oct. 9, 2012.
Restriction Requirement for U.S. Appl. No. 13/442,637, mailed May 17, 2012.
Response to Restriction Requirement for U.S. Appl. No. 13/442,637, filed Jun. 5, 2012.
Supplemental Response and Amendment for U.S. Appl. No. 13/442,637, filed Jun. 6, 2012.
Office Action for U.S. Appl. No. 13/442,637, mailed Aug. 9, 2012.
Response to Office Action for U.S. Appl. No. 13/442,637, filed Oct. 9, 2012.
Final Office Action for U.S. Appl. No. 13/442,637, mailed Dec. 20, 2012.
Response to Final Office Action for U.S. Appl. No. 13/442,637, filed Mar. 20, 2013.
Advisory Action for U.S. Appl. No. 13/442,637, mailed Apr. 1, 2013.
Preliminary Amendment and remarks with filing of RCE for U.S. Appl. No. 13/442,637, filed Apr. 17, 2013.
Invitation to Pay Additional Fees and, Where Applicable, Protest Fee for PCT/US2012/032759, mailed Jul. 16, 2012.
International Search Report and Written Opinion for PCT/US2012/032759, mailed Sep. 28, 2012.
International Preliminary Report on Patentability Chapter I for PCT/US2012/032759, issued Oct. 8, 2013.
Anderson et al., "Microarrayed Compound Screening to Identify Activators and Inhibitors of AMP-Activated Protein Kinase," J. of Biomolecular Screening (2004) 9:112 POI:0.1177/1087057103260592.
Angenendt et al., "Cell-free expression and functional assay in a nanowell chip format," Analytical Chemistry (2004) 76(7):1844-49.
Angenendt et al.,"Generation of High Density Protein Microarrays by Cell-free in Situ Expression of Unpurified PCR Products," Molecular and Cellular Proteomics, (2006) Ch. 5.9, pp. 1658-1666.
Atkinson, Overview of Translation: Lecture Manuscript, U of Texas (2000) pp. 6.1-6.8.
Burns et al., "Well-less, gel-permeation formats for ultra-HTS," DDT (2001) 6(12):S40-S47.
Carlson et al., "Formylglycine-generating Enzyme," J. of Biological Chemistry (2008) 283(29):20117-125.
Cha and Tilly, "Specificity, Efficiency and Fidelity of PCR," Genome Res. (1993) 3:518-29.
Chatterjee et al., "Microarray System," PLos One (2008) 3(9):e3265.
Darmanis, et al., "ProteinSeq: High-Performance Proteomic Analyses by Proximity, Ligation and Next Generation Sequencing", PLos One (2011) 6(9):e25583 doi1 0.1371/journal.pone.0025583 20 1.

(56) References Cited

OTHER PUBLICATIONS

Fredriksson et al., "Multiplexed proximity ligation assays to profile putative plasma biomarkers relevant to pancreatic and ovarian cancer," Clin. Chem. (2008) 5 (3):582-89.
Frese and Dierks, "Formylglycine Aldehyde Tag-Protein Engineering through a Novel Post-translational Modification," ChemBioChem (2009) 10:425-27.
Fu et al., "Counting individual DNA molecules by the stochastic attachment of diverse labels," PNAS (2011) 108:9026-9031.
He et al., "In situ synthesis of protein arrays," Current Opinion in Biotechnology (2008) 19:4-9.
He et al., "In situ synthesis of protein arrays," Current Opinion in Biotechnology (2008)19:4-9 Supplementary figures.
He, "Cell-free protein synthesis: applications in proteomics and biotechnology," (2008) New Biotechnology 25:126-132.
He et al., "Printing protein arrays from DNA arrays," Nature Methods (2008) 5:175-77.
Hedskog et al., "Dynamics of HIV-1 Quasispecies during Antiviral Treatment Dissected using Ultra-Deep Pyrosequencing," PLoS One (2010) 5(7)e11345.
Hendrickson et al., "High sensitivity multianalyte immunoassay using covalent DNA-labeled antibodies and polymerase chain reaction," Nucl. Acid Res. (1995) 23(9):522-29.
Hiatt et al., "Parallel, tag-directed assembly of locally-derived short sequence reads," Nature Methods (2010) 7(2):119-25.
Kozlov et al., "A Method for Rapid Protease Substrate Evaluation and Optimization," Comb. Chem. and High Throughput (2006) 9:481-87.
Kozlov et al., "A Highly Scalable Peptide-Based Assay System for Proteomics," PLoS ONE (2012) 7(6):e37441.
Kurz et al., "cDNA-Protein Fusions: Covalent Protein-Gene Conjugates for the In Vitro Selection of Peptides and Proteins," ChemBioChem (2001) 2:666-72.
Larman et al., "Autoantigen discovery with a synthetic human peptidome", Nature Biotechnology (2011) doi:1 0.1038/nbt.1856.
Lundberg et al.,"Homogeneous antibody-based proximity extension assays provide sensitive and specific detection of low-abundant proteins in human blood", Nucleic Acids Res. (2011) 39(15):e1 02 (Abstract).
Ng et al., "Massively parallel sequencing and rare disease," Human Molec. Genetics (2010) 19(2):R119-R124.
Oleinikov et al. "Self-assembling protein arrays using electronic semiconductor microchips and in vitro translation," Journal of Proteome Research (2003) 2:313-319.
Roberts and Szostak, "RNA-peptide fusions for the in vitro selection of peptides and proteins," PNAS USA (1997) 94:12297-302.
Rouillard et al., "OligoArray 2.0: design of oligonucleotide probes for DNA microarrays using a thermodynamic approach," Nuc. Acid Research (2003) 31 (12):3057-62.
Rush and Bertozzi, "New Aldehyde Tag Sequences Identified by Screening Formylglycine Generating Enzymes in Vitro and in Vivo," J. of American Chemical Society (2008) 130:12240-41.
Rush and Bertozzi, "New Aldehyde Tag Sequences Identified by Screening Formylglycine Generating Enzymes in Vitro and in Vivo," J. of American Chemical Society (2008) 130:12240-41 (2008) Supplement.
Schmitt et al., "Detection of ultra-rare mutations by next-generation sequencing," PNAS (2012) 109:14508-14523.
Takahashi and Roberts, "In Vitro Selection of Protein and Peptide Libraries Using mRNA Display," Nucleic Acid and Peptide Aptamers: Methods and Protocols (2009) 535:293-314 (Ch.17).
Tolbert and Wong, "New Methods for Proteomic Research: Preparation of Proteins with N-Terminal Cysteines for Labeling and Conjugation," Angew. Chem. Int. Ed. (2012) 41 (12):2171-74.
Vogelstein and Kinzler, "Digital PCR," PNAS USA (1999) 96:9236-41.
Waichman et al., "Functional Immobilization and Patterning of Proteins by an Enzymatic Transfer Reaction", Anal. Chem. (2010) 82:1478-85.

Wong et al. "Direct Site-Selective Covalent Protein Immobilization Catalyzed by a Phosphopantetheinyl Transferase," J. Am. Chem Soc. (2008) 130:12456-64.
Xiao et al., "Direct determination of haplotypes from single DNA molecules," Nature Methods (2009) 6(3):199-01.
Yin et al., "Genetically encoded short peptide tag for versatile protein labeling by Sfp phosphopantetheinyl transferase," PNAS (2005) 102(44):15815-20.
Zhou et al., "Genetically Encoded Short Peptide Tags for Orthogonal Protein Labeling by Sfp and AcpS Phosphopentetheinyl Transferases," ACS Chemical Biology (2007) 2(5): 374-346.
Zlobec et al., "Next-generation tissue microarray (ngTMA) increases the quality of biomarker studies: an example using CD3, CD8, and CD45RO in the tumor microenvironment of six different solid tumor types," Journal of Translational Medicine (2013) 11:104.
Blokzijl et al., "Profiling protein expression and interactions: proximity ligation as a tool for personalized medicine," J Intern Med (2010) 268:232-245.
Cheng et al., "Sensitive Detection of Small Molecules by Competitive Immunomagnetic-Proximity Ligation Assay," Anal Chem (2012) 84:2129-2132.
Ellington et al., "Antibody-based protein multiplex platforms: technical and operational challenges," Clin Chem (2010) 56(2):186-193.
European Search Report for EP 11766613.1, dated Jan. 15, 2014, 5 pages.
Final Office Action for U.S. Appl. No. 13/266,568, mailed Dec. 5, 2013, 7 pages.
Flanigon et al., "Multiplex protein detection with DNA readout via mass spectrometry," N Biotechnol (2013) 30(2):153-158.
Gu et al., "Protein tag-mediated conjugation of oligonucleotides to recombinant affinity binders for proximity ligation," N Biotechnol (2013) 30(2):144-152.
Hammond et al., "Profiling cellular protein complexes by proximity ligation with dual tag microarray readout," (2012) 7(7):e40405.
Mir et al., "Sequencing by cyclic ligation and cleavage (CycLiC) directly on a microarray captured template," Nucleic Acids Research (2009) 37(1):e5-1.
Lundberg et al., "Multiplexed homogeneous proximity ligation assays for high-throughput protein biomarker research in serological material," Mol Cell Proteomics (2011) 10(4):M110.004978.
Patent Examination Report No. 1 for AU2011237729, issued Jul. 15, 2013, 3 pages.
Preliminary Amendment for U.S. Appl. No. 14/068,921, filed Nov. 22, 2013, 10 pages.
Proseek® Multiplex 96x96 User Manual (2013) Olink Bioscience, Uppsala, Sweden, 20 pages.
Response to First Examination Report for EP 10836568.5-1403, filed Feb. 17, 2014, 10 pages.
Zhang et al., "Assembling DNA through Affinity Binding to Achieve Ultrasensitive Protein Detection," Angew Chem Int Ed (2013) 52:2-10.
Zhang et al., "Binding-induced DNA assembly and its application to yoctomole detection of proteins," Anal Chem (2012) 84(2):877-884.
Response After Final Office Action for U.S. Appl. No. 13/266,568, filed Mar. 4, 2014.
Response to Patent Examination Report No. 1 for AU 2011237729, filed Mar. 3, 2014.
Notice of Acceptance issued in Australian Patent Application No. AU 2011237729, dated Mar. 20, 2014, 6 pages.
Examination Report issued in European Patent Application No. 10836568.5, dated Mar. 12, 2014, 3 pages.
Mizusawa and Ward et al., "A bacteriophage lambda vector for cloning with BamHl and Sau3A," Gene (1982) 20(3):317-322.
Shoemaker et al., "Quantitative phenotypic analysis of yeast deletion mutants using a highly parallel molecular bar-coding strategy," Nat Genet (1996) 14(4):450-456.
Worthington et al., "Cloning of random oligonucleotides to create single-insert plasmid libraries," Anal Biochem (2001) 294(2):169-175.
Office Action for U.S. Appl. No. 13/266,568, mailed Mar. 26, 2014, 9 pages.
Response to Office Action for U.S. Appl. No. 13/266,568, dated Jun. 26, 2014, 11 pages.

(56) References Cited

OTHER PUBLICATIONS

Patent Examination Report No. 1 for AU 2010278710, issued Feb. 11, 2014, 4 pages.
Examination Report for European Patent Application No. EP 10836568.5, dated Mar. 12, 2014, 3 pages.
Response to Examination Report for European Patent Application No. EP 10836568.5, dated Jul. 10, 2014, 1 page.
Office Action for Canadian Patent Application No. 2794522, issued May 22, 2014, 4 pages.
Response to Search Report for European Patent Application No. EP 11766613.1, dated Jul. 11, 2014, 1 page.
Response to Office Action for CA 2794522, dated Sep. 17, 2014.
European Examination Report for EP 11766613.1, dated Aug. 22, 2014.
Response to European Examination Report for EP 11766613.1, filed Jan. 8, 2015.
Office Action for U.S. Appl. No. 13/442,637, mailed Jan. 22, 2015.
Extended European Search Report for EP 12767937.1-1403, mailed Nov. 18, 2014.
International Search Report and Written Opinion of PCT/US14/29691, mailed Aug. 19, 2014.
International Search Report and Written Opinion of PCT/US14/44191, mailed Nov. 7, 2014.
International Search Report and Written Opinion of PCT/US14/44196, mailed Nov. 7, 2014.
International Search Report and Written Opinion of PCT/US14/64588, mailed Mar. 11, 2015.
Alexander Valencia et al., "mRNA-display-based selections for proteins with desired functions: A protease-substrate case study," Biotechnology Progress, 2008, 24(3):561-569.
Osada et al., "Epitope mapping using ribosome display in a resconstituted cell-free protein synthesis system," Journal of Biochemistry, 2009, 145(5):693-700.
Rountenberg et al., "Microfluidic probe: a new tool for integrating microfluidic environments and electronic wafer-probing," Lab Chip, Oct. 29, 2009, 10: 123-127.
Weichhart et al., "Functional selection of vaccine candidate peptides from *Staphylococcus aureus* whole-genome expression libraries in vitro," Infection and Immunity, 2003, 71(8):4333-4641.

\* cited by examiner

SPATIALLY ENCODED BIOLOGICAL ASSAYS

CROSS-REFERENCE TO RELATED APPLICATIONS

This application claims the benefit of U.S. Provisional Patent Application No. 61/321,124, filed Apr. 5, 2010 and is incorporated herein by reference.

This invention was made with government support under 1R43GM096706 awarded by the National Institute of General Medical Sciences division of the National Institutes of Health. The government has certain rights in the invention.

FIELD OF THE INVENTION

This invention relates to assays of biological molecules, and more particularly to assays for determining spatial distributions of a large number of biological molecules in a solid sample simultaneously.

BACKGROUND OF THE INVENTION

In the following discussion certain articles and methods will be described for background and introductory purposes. Nothing contained herein is to be construed as an "admission" of prior art. Applicant expressly reserves the right to demonstrate, where appropriate, that the articles and methods referenced herein do not constitute prior art under the applicable statutory provisions.

Comprehensive gene expression analysis and protein analysis have been useful tools in understanding mechanisms of biology. Use of these tools has allowed the identification of genes and proteins involved in development and in various diseases such as cancer and autoimmune disease. Conventional methods such as in situ hybridization and other multiplexed detection of different transcripts have revealed spatial patterns of gene expression and have helped shed light on the molecular basis of development and disease. Other technologies that have enabled the quantitative analysis of many RNA sequences per sample include microarrays (see Shi, et al., Nature Biotechnology, 24(9):1151-61 (2006); and Slonim and Yanai, Plos Computational Biology, 5(10):e1000543 (2009)); serial analysis of gene expression (SAGE) (see Velculescu, et al., Science, 270(5235):484-87 (1995)), high-throughput implementations of qPCR (see Spurgeon, et al., Plos ONE, 3(2):e1662 (2008)) and in situ PCR (see Nuovo, Genome Res., 4:151-67 (1995)). As useful as these methods are, however, they do not enable simultaneous measurement of the expression of many genes or the presence and/or activity of multiple proteins at many spatial locations in a sample. Laser capture microdissection has permitted the analysis of many genes at a small number of locations, but it is very expensive, laborious, and does not scale well. Certain PCR assays in a 2D format preserve spatial information (see Armani, et al., Lab on a Chip, 9(24):3526-34 (2009)), but these methods have low spatial resolution because they rely on physical transference of tissue into wells, which also prevents random access to tissue samples and high levels of multiplexing.

At present, no practical method exists to analyze at high resolution the spatial expression patterns of large numbers of genes, proteins, or other biologically active molecules simultaneously. There is thus a need for reproducible, high-resolution spatial maps of biological molecules in tissues. The present invention addresses this need.

SUMMARY OF THE INVENTION

This Summary is provided to introduce a selection of concepts in a simplified form that are further described below in the Detailed Description. This Summary is not intended to identify key or essential features of the claimed subject matter, nor is it intended to be used to limit the scope of the claimed subject matter. Other features, details, utilities, and advantages of the claimed subject matter will be apparent from the following written Detailed Description including those aspects illustrated in the accompanying drawings and defined in the appended claims.

The invention encompasses assay systems that provide high-resolution spatial maps of biological activity in tissues. The assay system comprises an assay capable of high levels of multiplexing where encoded probes are provided to a biological sample in defined spatial patterns; instrumentation capable of controlled delivery of reagents according to the spatial patterns; and a decoding scheme providing a readout that is digital in nature. In short, the present invention provides the ability to look at many biological targets in many locations, providing the resolution of in situ hybridization with the highly-parallel data analysis of sequencing.

Thus, in some embodiments, the invention provides an assay system to determine spatial patterns of abundance or activity or both of multiple biological targets at multiple sites in a sample, where the assay system performs the following steps: providing a sample affixed to a support; delivering encoded probes for the multiple biological targets to the multiple sites in the sample in a known spatial pattern, where each encoded probe comprises a probe region that may interact with the biological targets and a coding tag that identifies a location of the site to which the encoded probe was delivered; allowing the encoded probes to interact with the biological targets; separating encoded probes that interact with the biological targets from encoded probes that do not interact with the biological targets; determining all or a portion of a sequence of the encoded probes, and associating the abundance or activity or both of the multiple biological targets to the locations of the sites in the sample.

In particular aspects of the invention the biological targets comprise nucleic acids and the encoded probes are oligonucleotides, and in some aspects, there are two encoded probes for each of the multiple nucleic acid targets. In some aspects, the multiple biological targets comprise proteins, the probe regions of the encoding probes are proteins and the coding tags comprise oligonucleotides. In some aspects the multiple biological targets comprise enzymes. In some aspects the probe regions of the encoded probes comprise antibodies, aptamers or small molecules.

Some aspects of the assay system further comprise an amplification step between the separating step and the determining step. In some aspects, the determining step is performed by nucleic acid sequencing, and in preferred aspects, the sequencing is high-throughput digital nucleic acid sequencing.

In some aspects of the invention, the product of the multiple biological targets being assayed and the multiple sites in the sample is greater than 20, in some aspects product of the multiple biological targets being assayed and the multiple sites in the sample is greater than 50, in some aspects the product of the multiple biological targets being assayed and the multiple sites in the sample is greater than 75, 100, 150, 500, 750, 1,000, 5,000, 10,000, 25,000, 50,000, 100,000, 500,000, or 1,000,000 or more. In other aspects, the sequence of at least fifty thousand encoding probes are determined in parallel, in other aspects the sequence of at least one hundred thousand encoding probes are determined in parallel, in some aspects the sequence of at least five hundred thousand encoding probes are determined in parallel, and in some aspects the sequence of at least one million, ten million, one hundred million, one billion, ten billion, one hundred billion or more encoding probes are determined in parallel.

In some aspects, the known spatial pattern is determined by histological features of the sample. Also in some aspects, software programmed hardware performs at least two steps of the delivering step, the separation step, the determining step and the associating step.

In some aspects, the probe regions of the encoded probes are proteins and the separating step is accomplished by encoded probes that interact with the biological targets being captured by an affinity capture agent. In some aspects the probe regions of the encoding probes are nucleic acids and the separating step is accomplished by a washing of the sample.

In other embodiments there is provided an assay system to determine spatial patterns of abundance or activity or both of multiple nucleic acid targets at multiple sites in a sample, where the assay system performs the following steps: providing a sample affixed to a support; delivering oligonucleotide probes for multiple nucleic acid targets to the multiple sites in the sample in a known spatial pattern; allowing the oligonucleotide probes to hybridize with the nucleic acid targets; washing unhybridized encoded oligonucleotide probes from the sample; delivering one or more encoding agents to locations of the multiple sites in the sample according to a known spatial pattern, where the combination of encoding agents delivered to each site is different; coupling the encoding agents and the oligonucleotide probes to form encoded probes; determining all or a portion of a sequence of the encoded probes using high-throughput sequencing, and associating the abundance or activity or both of multiple biological targets to the locations of multiple sites in the sample.

Other embodiments of the invention provide an assay system to determine spatial patterns of abundance or activity or both of multiple protein targets at multiple sites in a sample, where the assay system performs the following steps: providing a sample affixed to a support; delivering encoded probes for the multiple protein targets to the multiple sites in the sample in a known spatial pattern, where each encoded probe comprises a protein probe region that may interact with the protein targets and a coding tag that identifies a location of the site to which the encoded probe was delivered and the protein probe region of the encoding probe of which the coding tag is part; allowing the encoded probes to interact with the protein targets; separating encoded probes that interact with the protein targets from encoded probes that do not interact with the protein targets; determining all or a portion of a sequence of the encoded probes by high throughput sequencing, and associating the abundance or activity or both of the multiple protein targets to the locations of the multiple sites in the sample.

Other embodiments provide an assay system to determine spatial patterns of abundance or activity or both of multiple biological targets at multiple sites in a sample, where the assay system performs the following steps: providing a sample affixed to a support; delivering encoded probes for the multiple biological targets to the multiple sites in the sample in a known spatial pattern, where each encoded probe comprises a probe region that may interact with the biological targets and a coding tag that identifies a location of the site to which the encoded probe was delivered and identifies the biological target; allowing the encoded probes to interact with the biological targets; determining all or a portion of a sequence of the encoded probes, and associating the abundance or activity or both of the multiple biological targets to the locations of the sites in the sample.

The assay system of the invention can utilize various detection mechanisms, based on the molecules to be detected and the reagents needed for such detection system. Exemplary methods that can be used with the assay systems of the invention are described in more detail below.

DESCRIPTION OF THE FIGURES

FIG. 4A shows two target-specific/encoding oligonucleotide constructs specifically bound to a target nucleic acid of interest in a sample. FIG. 4B shows a scheme for delivering twenty different coding tags, a1 through a10 and b1 through b10, to a sample to form a 10×10 coding tag grid. FIG. 4C shows a tissue section sample which the coding tags are delivered, forming the coding tag grid in the sample.

DEFINITIONS

Figure 1:
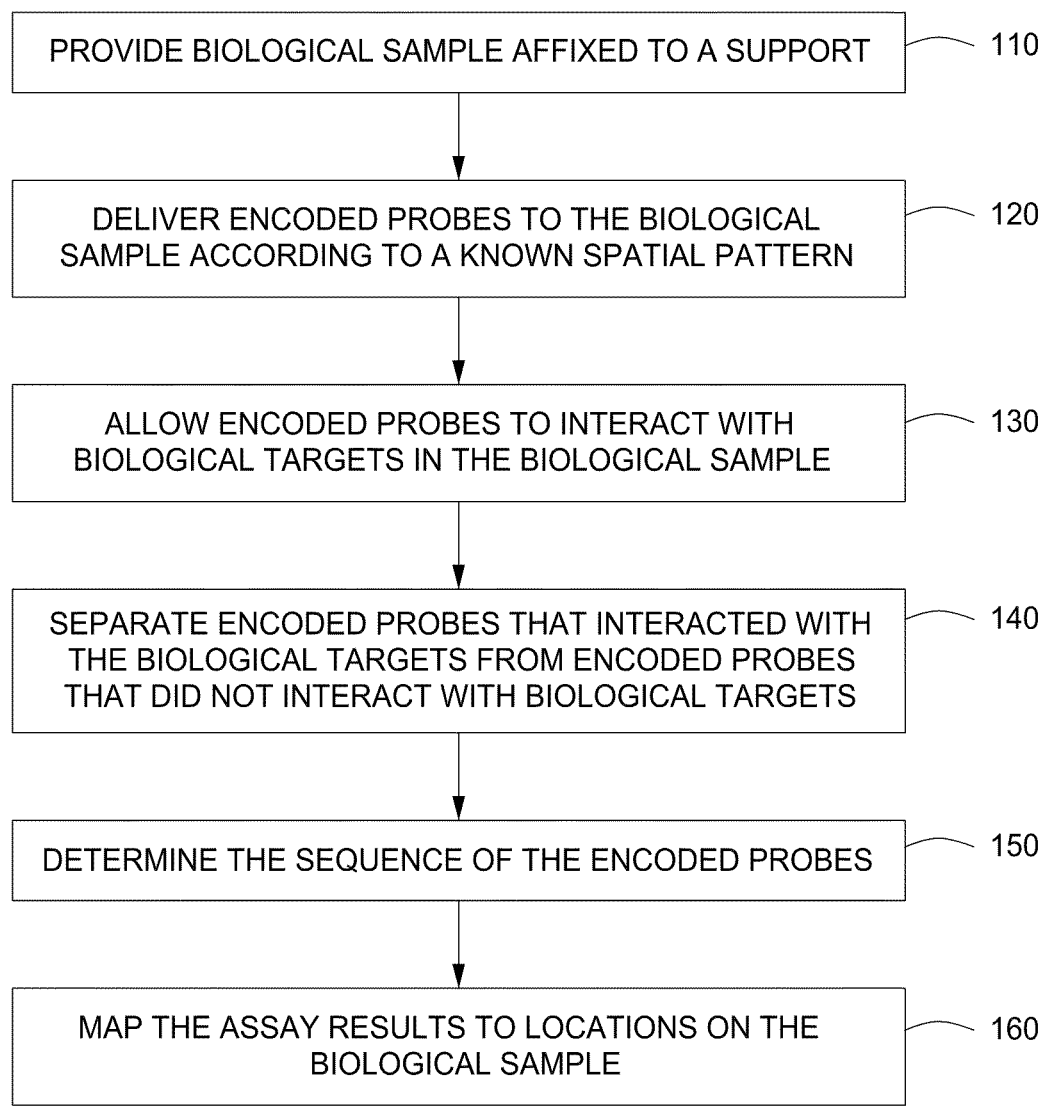
FIG. 1 provides a simplified overview of the assay system of the present invention.

The terms used herein are intended to have the plain and ordinary meaning as understood by those of ordinary skill in the art. The following definitions are intended to aid the reader in understanding the present invention, but are not intended to vary or otherwise limit the meaning of such terms unless specifically indicated.

The term "antibody" as used herein is intended to refer to an entire immunoglobulin or antibody or any functional fragment of an immunoglobulin molecule which is capable of specific binding to an antigen (antibodies and antigens are "binding partners" as defined herein). "Antibody" as used herein is meant to include the entire antibody as well as any antibody fragments capable of binding the antigen or antigenic fragment of interest. Examples of such peptides include complete antibody molecules, antibody fragments, such as Fab, F(ab')2, CDRS, VL, VH, and any other portion of an antibody which is capable of specifically binding to an antigen. Antibodies for assays of the invention are immunoreactive or immunospecific for, and therefore specifically and selectively bind to, proteins either detected (i.e., biological targets) or used for detection (i.e., probes) in the assays of the invention.

The term "binding agent" as used herein refers to any agent that specifically binds to a biological molecule of interest.

"Complementary" or "substantially complementary" refers to the hybridization or base pairing or the formation of a duplex between nucleotides or nucleic acids, such as, for instance, between the two strands of a double-stranded DNA molecule or between an oligonucleotide primer and a primer binding site on a single-stranded nucleic acid. Complementary nucleotides are, generally, A and T (or A and U), or C and G. Two single-stranded RNA or DNA molecules are said to be substantially complementary when the nucleotides of one strand, optimally aligned and compared and with appropriate nucleotide insertions or deletions, pair with at least about 80% of the other strand, usually at least about 90% to about 95%, and even about 98% to about 100%.

"Hybridization" refers to the process in which two single-stranded polynucleotides bind non-covalently to form a stable double-stranded polynucleotide. The resulting (usually) double-stranded polynucleotide is a "hybrid" or "duplex." "Hybridization conditions" will typically include salt concentrations of approximately less than 1 M, often less than about 500 mM and may be less than about 200 mM. A "hybridization buffer" is a buffered salt solution such as 5% SSPE, or other such buffers known in the art. Hybridization temperatures can be as low as 5° C., but are typically greater than 22° C., and more typically greater than about 30° C., and typically in excess of 37° C. Hybridizations are often performed under stringent conditions, i.e., conditions under which a primer will hybridize to its target subsequence but will not hybridize to the other, non-complementary sequences. Stringent conditions are sequence-dependent and are different in different circumstances. For example, longer fragments may require higher hybridization temperatures for specific hybridization than short fragments. As other factors may affect the stringency of hybridization, including base composition and length of the complementary strands, presence of organic solvents, and the extent of base mismatching, the combination of parameters is more important than the absolute measure of any one parameter alone. Generally stringent conditions are selected to be about 5° C. lower than the $T_m$ for the specific sequence at a defined ionic strength and pH. Exemplary stringent conditions include a salt concentration of at least 0.01 M to no more than 1 M sodium ion concentration (or other salt) at a pH of about 7.0 to about 8.3 and a temperature of at least 25° C. For example, conditions of 5×SSPE (750 mM NaCl, 50 mM sodium phosphate, 5 mM EDTA at pH 7.4) and a temperature of approximately 30° C. are suitable for allele-specific hybridizations, though a suitable temperature depends on the length and/or GC content of the region hybridized.

"Ligation" means to form a covalent bond or linkage between the termini of two or more nucleic acids, e.g., oligonucleotides and/or polynucleotides, in a template-driven reaction. The nature of the bond or linkage may vary widely and the ligation may be carried out enzymatically or chemically. As used herein, ligations are usually carried out enzymatically to form a phosphodiester linkage between a 5' carbon terminal nucleotide of one oligonucleotide with a 3' carbon of another nucleotide.

"Nucleic acid", "oligonucleotide", "oligo" or grammatical equivalents used herein refers generally to at least two nucleotides covalently linked together. A nucleic acid generally will contain phosphodiester bonds, although in some cases nucleic acid analogs may be included that have alternative backbones such as phosphoramidite, phosphorodithioate, or methylphophoroamidite linkages; or peptide nucleic acid backbones and linkages. Other analog nucleic acids include those with bicyclic structures including locked nucleic acids, positive backbones, non-ionic backbones and non-ribose backbones. Modifications of the ribose-phosphate backbone may be done to increase the stability of the molecules; for example, PNA:DNA hybrids can exhibit higher stability in some environments.

"Primer" means an oligonucleotide, either natural or synthetic, that is capable, upon forming a duplex with a polynucleotide template, of acting as a point of initiation of nucleic acid synthesis and being extended from its 3' end along the template so that an extended duplex is formed. The sequence of nucleotides added during the extension process is determined by the sequence of the template polynucleotide. Primers usually are extended by a DNA polymerase.

The term "SNP" or "single nucleotide polymorphism" refers to a genetic variation between individuals; e.g., a single nitrogenous base position in the DNA of organisms that is variable. SNPs are found across the genome; much of the genetic variation between individuals is due to variation at SNP loci, and often this genetic variation results in phenotypic variation between individuals. SNPs for use in the present invention and their respective alleles may be derived from any number of sources, such as public databases (U.C. Santa Cruz Human Genome Browser Gateway (http://genome.ucsc.edu/cgi-bin/hgGateway) or the NCBI dbSNP website (http://www.ncbi.nlm.nih.gov/SNP/), or may be experimentally determined as described in U.S. Pat. No. 6,969,589; and US Pub. No. 2006/0188875 entitled "Human Genomic Polymorphisms." Although the use of SNPs is described in some of the embodiments presented herein, it will be understood that other biallelic or multi-allelic genetic markers may also be used. A biallelic genetic marker is one that has two polymorphic forms, or alleles. As mentioned above, for a biallelic genetic marker that is associated with a trait, the allele that is more abundant in the genetic composition of a case group as compared to a control group is termed the "associated allele," and the other allele may be referred to as the "unassociated allele." Thus, for each biallelic polymorphism that is associated with a given trait (e.g., a disease or drug response), there is a corresponding associated allele. Other biallelic polymorphisms that may be used with the methods presented herein include, but are not limited to multinucleotide changes, insertions, deletions, and translocations. It will be further appreciated that references to DNA herein may include genomic DNA, mitochondrial DNA, episomal DNA, and/or derivatives of DNA such as amplicons, RNA transcripts, cDNA, DNA analogs, etc. The polymorphic loci that are screened in an association study may be in a diploid or a haploid state and, ideally, would be from sites across the genome.

The term "selectively binds", "selective binding" and the like as used herein, when referring to a binding partner (e.g., protein, nucleic acid, antibody or other affinity capture agent, etc.), refers to a binding reaction of two or more binding partners with high affinity and/or complementarity to ensure selective hybridization under designated assay conditions. Typically, specific binding will be at least three times the standard deviation of the background signal. Thus, under designated conditions the binding partner binds to its particular "target" molecule and does not bind in a significant amount to other molecules present in the sample.

"Sequencing", "sequence determination" and the like means determination of information relating to the nucleotide base sequence of a nucleic acid. Such information may include the identification or determination of partial as well as full sequence information of the nucleic acid. Sequence information may be determined with varying degrees of statistical reliability or confidence. In one aspect, the term includes the determination of the identity and ordering of a plurality of contiguous nucleotides in a nucleic acid. "High throughput digital sequencing" or "next generation sequencing" means sequence determination using methods that determine many (typically thousands to billions) of nucleic acid sequences in an intrinsically parallel manner, i.e. where DNA templates are prepared for sequencing not one at a time, but in a bulk process, and where many sequences are read out preferably in parallel, or alternatively using an ultra-high throughput serial process that itself may be parallelized. Such methods include but are not limited to pyrosequencing (for example, as commercialized by 454 Life Sciences, Inc., Branford, Conn.); sequencing by ligation (for example, as commercialized in the SOLiD™ technology, Life Technology, Inc., Carlsbad, Calif.); sequencing by synthesis using modified nucleotides (such as commercialized in TruSeq™ and HiSeq™ technology by Illumina, Inc., San Diego, Calif., HeliScope™ by Helicos Biosciences Corporation, Cambridge, Ma., and PacBio RS by Pacific Biosciences of California, Inc., Menlo Park, Calif.), sequencing by ion detection technologies (Ion Torrent, Inc., South San Francisco, Calif.); sequencing of DNA nanoballs (Complete Genomics, Inc., Mountain View, Calif.); nanopore-based sequencing technologies (for example, as developed by Oxford Nanopore Technologies, LTD, Oxford, UK), and like highly parallelized sequencing methods.

The term "$T_m$" is used in reference to the "melting temperature." The melting temperature is the temperature at which a population of double-stranded nucleic acid molecules becomes half dissociated into single strands. Several equations for calculating the $T_m$ of nucleic acids are well known in the art. As indicated by standard references, a simple estimate of the $T_m$ value may be calculated by the equation, $T_m=81.5+0.41$ (% G+C), when a nucleic acid is in aqueous solution at 1 M NaCl (see e.g., Anderson and Young, Quantitative Filter Hybridization, in *Nucleic Acid Hybridization* (1985)). Other references (e.g., Allawi and SantaLucia, Jr., Biochemistry, 36:10581-94 (1997)) include alternative methods of computation which take structural and environmental, as well as sequence characteristics into account for the calculation of $T_m$.

DETAILED DESCRIPTION OF THE INVENTION

The practice of the techniques described herein may employ, unless otherwise indicated, conventional techniques and descriptions of organic chemistry, polymer technology, molecular biology (including recombinant techniques), cell biology, biochemistry, and sequencing technology, which are within the skill of those who practice in the art. Such conventional techniques include polymer array synthesis, hybridization and ligation of polynucleotides, and detection of hybridization using a label. Specific illustrations of suitable techniques can be had by reference to the examples herein. However, other equivalent conventional procedures can, of course, also be used. Such conventional techniques and descriptions can be found in standard laboratory manuals such as Green, et al., Eds., *Genome Analysis: Laboratory Manual Series* (Vols. I-IV) (1999); Weiner, Gabriel, Stephens, Eds., *Genetic Variation: A Laboratory Manual* (2007); Dieffenbach, Dveksler, Eds., *PCR Primer: A Laboratory Manual* (2003); Bowtell and Sambrook, *DNA Microarrays: A Molecular Cloning Manual* (2003); Mount, *Bioinformatics: Sequence and Genome Analysis* (2004); Sambrook and Russell, *Condensed Protocols from Molecular Cloning: A Laboratory Manual* (2006); and Sambrook and Russell, *Molecular Cloning: A Laboratory Manual* (2002) (all from Cold Spring Harbor Laboratory Press); Stryer, *Biochemistry* (4th Ed.) (1995) W. H. Freeman, New York N.Y.; Gait, "*Oligonucleotide Synthesis: A Practical Approach*" (2002) IRL Press, London; Nelson and Cox, *Lehninger, Principles of Biochemistry* (2000) $3^{rd}$ Ed., W. H. Freeman Pub., New York, N.Y.; and Berg, et al., *Biochemistry* (2002) $5^{th}$ Ed., W. H. Freeman Pub., New York, N.Y., all of which are herein incorporated in their entirety by reference for all purposes.

Note that as used herein and in the appended claims, the singular forms "a," "an," and "the" include plural referents unless the context clearly dictates otherwise. Thus, for example, reference to "a nucleic acid" refers to one or more nucleic acids, and reference to "the assay" includes reference to equivalent steps and methods known to those skilled in the art, and so forth.

Unless defined otherwise, all technical and scientific terms used herein have the same meaning as commonly understood by one of ordinary skill in the art to which this invention belongs. All publications mentioned herein are incorporated by reference for the purpose of describing and disclosing devices, formulations and methodologies that may be used in connection with the presently described invention.

Where a range of values is provided, it is understood that each intervening value, between the upper and lower limit of that range and any other stated or intervening value in that stated range is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either both of those included limits are also included in the invention.

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention.

The Invention in General

The assay systems of the invention provide spatially-encoded, multiplexed assays comprising 1) an assay capable of high levels of multiplexing with an efficient spatial encoding scheme; 2) instrumentation capable of delivering reagents according to a spatial pattern; and 3) decoding determined by a readout that is digital in nature. The assay systems of the invention detect the presence or absence and relative amount of a biological target or biological activity indicative of a biological target, as well as the location of the biological target or activity in a biological sample, e.g., a tissue section or other biological structure disposed upon a support such as a microscope slide or culture dish.

The assay system further provides instrumentation with an ability to deliver reagents in a spatially-defined pattern. This instrumentation, together with software, reagents and protocols, provides a key component of the highly innovative assay system of the invention, allowing for measurement of numerous biological targets or activities in a meaningful spatial environment, including gene expression and peptide localization. An encoding scheme used in these assay systems allows one to determine the location of biological targets or activity (or lack thereof) in the biological samples after the products of the multiplexed assay are removed from the biological sample and pooled for analysis. Decoding of the encoding scheme can be performed by, e.g., next-generation sequencing, which easily provides millions to trillions of datapoints at low cost. The assay results such as the amount or activity of biological targets can then be mapped back to specific location in the biological sample. The assay systems open a new analytical window into the complex spatial patterns of cellular function and regulation in biological samples.

A simplified overview of the assay system 100 of the present invention is provided at FIG. 1. At step 110, a biological sample affixed to a support is provided. The biological sample contains biological targets of interest. Biological targets can include any molecule of interest, such as nucleic acids (including, e.g, RNA transcripts, genomic DNA sequences, cDNAs, amplicons, or other nucleic acid sequences) and proteins, enzymes and the like. At step 120, encoded probes are delivered to the biological sample according to a known spatial pattern. Encoded probes comprise probes, which can interact with biological targets of interest, and coding tags, which identify the positions in the sample of the biological targets being assayed, and thus can be used to link assay results back to locations in the sample. Coding tags in most embodiments are oligonucleotides. However, coding tags may also be mass tags, fluorescent labels, or other moieties.

In some embodiments, the probe and coding tag portions of the encoded probe are pre-coupled before being delivered to the biological sample, For example, in the case where the encoded probes are oligonucleotides, both the probe and coding tag sequence can be synthesized as a single oligonucleotide. Alternatively, the probe and coding tag portions of the encoding probes can be synthesized or obtained separately and combined before delivery to the biological sample (e.g., two separate oligonucleotides can be synthesized and coupled by, e.g., ligation; or an antibody and an oligonucleotide can be prepared separately and conjugated before delivery to the biological sample). Also, as is described in FIGS. 2-5, the probes and the coding tags (in encoding oligonucleotides) are synthesized separately, and are delivered to the biological sample at different steps (e.g., probes first and coding tags thereafter, or vice versa) in the assay.

At step 130, the encoded probes are allowed to react or interact with the biological targets, i.e., conditions are provided to allow e.g., oligonucleotides to hybridize to nucleic acid targets, enzymes to catalyze reactions with protein targets, antibodies to bind epitopes, etc. In the case where the biological targets are nucleic acids, the encoded probes are typically oligonucleotides and hybridize to the target nucleic acids. In the case that the biological targets are proteins, the encoded probes typically are aptamers, small molecules, or oligonucleotide-conjugated proteins that interact with target proteins by binding to them or by reacting with them (that is, one of the proteins is a substrate for the other). Encoding oligonucleotides may be coupled to the probes (proteins) by conjugation, chemical or photo-crosslinking via suitable groups and the like.

Once encoded probes interact with the biological targets, the encoded probes that interacted with the biological targets must be separated from the encoded probes that did not interact with the biological targets at step 140. In the case where the biological targets are nucleic acids and the encoded probes are oligonucleotides, the separation can be accomplished by, e.g., washing the unhybridized encoded probes from the sample. Similarly, for other assays that are based on affinity binding, including those using aptamer, small molecule, and protein probes, washing steps can be used to remove low affinity binders. In the case where the probe is transformed via interaction with the target, e.g., in the case of a peptide, e.g., via cleavage by a protease or phosphorylation by a kinase, it is convenient to collect, all encoded probes—both encoded probes that interacted with the biological targets and were transformed and encoded probes that were not transformed. After collection or pooling, an antibody or other affinity capture agent can be used to capture probes that were transformed by addition of a moiety (e.g., a phosphate group). In cases where probes have been transformed via cleavage, the transformed probes can be separated, e.g., by capturing the non-transformed probes via a tag that is removed from the transformed probes during the transformation (e.g., by cleavage), or by adding a new tag at the site of cleavage.

Once the reacted (transformed) or interacted encoded probes are separated from the unreacted or un-interacted encoded probes, the sequence of the reacted and/or interacted encoded probes is determined at step 150 by, preferably, sequencing. The sequence of the encoded probes allows the mapping of the assay results at step 160 back to locations in the biological sample.

Figure 2:
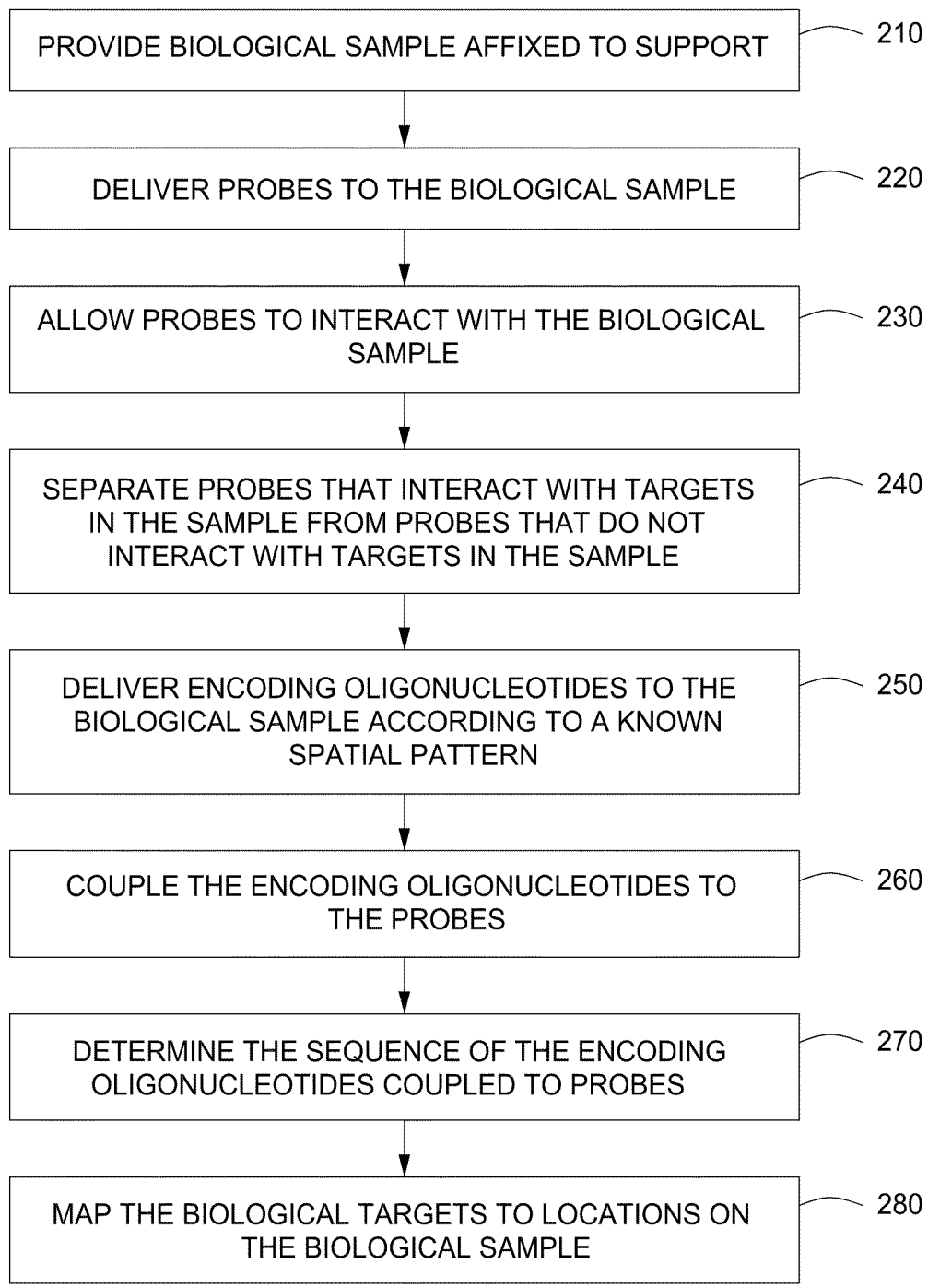
FIG. 2 provides a simplified overview of one embodiment of the assay system of the present invention for detecting nucleic acids.

FIG. 2 provides a simplified overview of an assay system 200 of the present invention embodying an efficient implementation of a combinatorial coding scheme for the encoding of spatial information. For purposes of this overview, the probes are oligonucleotides, but as explained elsewhere, other types of probes can also be used. In step 210, a biological sample affixed to a support, e.g., a tissue sample or other biological structure, is provided. In step 220, one or more oligonucleotide probes are delivered to the biological sample, where the oligonucleotide probes are capable of hybridizing with biological targets in the biological sample. In step 230, the oligonucleotide probes are allowed to interact with (hybridize to) the nucleic acid targets; that is, appropriate conditions are provided where oligonucleotide probes can hybridize to the target nucleic acids.

In step 240, the oligonucleotide probes that did not hybridize to target nucleic acids are removed, and thereby separated from oligonucleotide probes that did hybridize to target nucleic acids. In this embodiment, separation can be accomplished by, e.g., washing the sample to remove unhybridized oligonucleotide probes. Next, in step 250, encoding oligonucleotides (the encoding agents) are delivered to the biological sample according to a chosen spatial pattern, where the encoding oligonucleotides comprise coding tags that are used to encode the location of biological targets in the biological sample. Note that in contrast to the assay system of FIG. 1, here the probes and encoding agents (encoding oligonucleotides) are delivered in separate steps. In step 260, the encoding oligonucleotides are coupled to the oligonucleotide probes to create encoded probes. In this case where the probes are oligonucleotides, the encoding oligonucleotides may be coupled to the oligonucleotides probes by, e.g., ligation. Alternatively, the information in the encoding oligonucleotides can be transferred by using a DNA polymerase to extend a probe oligonucleotide that acts as a primer, and thereby copy and incorporate the sequence of the encoding oligonucleotides.

In step 270, the sequence of the coding tags in the encoded probes as well as the sequence or a portion of the sequence of the probe itself is determined, and in step 280, the target nucleic acids are mapped back to the biological sample. In some embodiments, the abundance of sequences reveals the relative quantity of biological targets at the location. Although this embodiment shows the individual steps in a particular order, so as to better explain the invention, the precise order of the steps can be varied. For example, steps 220 and 250 can be combined, so that a mixture of the probes and encoding oligonucleotides is delivered according to a chosen spatial pattern. Coupling step 260 can then be carried out immediately after the combined steps 220 and 250, or concomitantly with them. In this case, step 240 would then occur after step 260. It can therefore be appreciated that the two key results of this series of steps, i.e., the location-specific encoding of probe molecules and the separation of probe molecules based on their ability to interact with corresponding target molecules, can be accomplished with some flexibility in the implementation of the particular steps. Similarly, there is considerable flexibility in the design of the coding scheme. As described infra, the assays of the invention are particularly amenable to combinatorial methods.

Thus, the present invention provides an ability to look at many different biological targets in many locations, providing the resolution of in situ hybridization with the highly-parallel data analysis of sequencing. In some embodiments, the sum of the multiple biological targets being assayed and the multiple sites in the biological sample is greater than 20, in other embodiments, the sum of the multiple biological targets being assayed and the multiple sites in the biological sample is greater than 50, in other embodiments, the sum of the multiple biological targets being assayed and the multiple sites in the biological sample is greater than 100, greater than 500, 1,000, 10,000, 25,000, 100,000, 500,000, 1,000,000. It will be appreciated that, due to the spatial encoding dimension of the invention, even much larger numbers can be contemplated. For example, assaying 10,000 targets per location×10,000 locations would generate $10^8$ different assays, and even larger numbers than these can easily be contemplated, particularly if spatial locations with resolution on the order of that of single cells are utilized. Further, in embodiments where high-throughput digital sequencing is employed, the sequences of at least 1,000 encoding probes are typically determined in parallel. More typically, using a digital readout, it is desirable to obtain multiple sequence reads for each assay (defined by a probe and a spatial location code). It is desirable to obtain an average of at least 3 copies per assay, and more typically at least 10 or at least 30 copies per assay, depending on the design of the experiment and requirements of the assay. For a quantitative readout with suitable dynamic range, it may be desirable to obtain at lest 1,000 reads per assay. Therefore, if 1,000,000 assays are carried out, the number of sequence reads may be 1 billion or more. With high-throughput digital sequencing, and allowing for redundnacy, the sequence of at least 10,000 encoding probes are determined in parallel, or the sequence of at least 100,000, 500,000, 1,000,000, 10,000,000, 100,000,000, 1,000,000,000 or more encoding probes are determined in parallel.

Assays

The assay portion of the assay systems of the present invention comprise the following general steps: delivering probes and encoding agents where the encoding agents (in some embodiments pre-coupled to the probes) are delivered to the sample according to a known spatial pattern, allowing the probes to interact or react with biological targets in the sample, and, if the probes and encoding agents have not been pre-coupled, coupling the encoding agents to probes.

The samples of the present invention include virtually any biological sample or samples that can be affixed to a support or provided essentially in a two-dimensional manner, where the ability to tie an assayed biological target or activity back to the location within the biological sample is important. Exemplary biological samples include tissue sections (e.g., including whole animal sectioning and tissue biopsies), cell populations on slides or culture dishes, and the like. The assay systems of the invention are particularly advantageous in that they are compatible with numerous biological sample types, including fresh samples, such as primary tissue sections, and preserved samples including but not limited to frozen samples and paraformalin-fixed, paraffin-embedded (FFPE) samples. An important aspect of the assay systems of the invention is that the biological samples are immobilized on a substrate surface having discrete, independently measureable areas.

The biological targets to be detected can be any biological molecules including but not limited to proteins, nucleic acids, lipids, carbohydrates, ions, or multicomponent complexes containing any of the above. Examples of subcellular targets include organelles, e.g., mitochondria, Golgi apparatus, endoplasmic reticulum, chloroplasts, endocytic vesicles, exocytic vesicles, vacuoles, lysosomes, etc.

Figure 3:
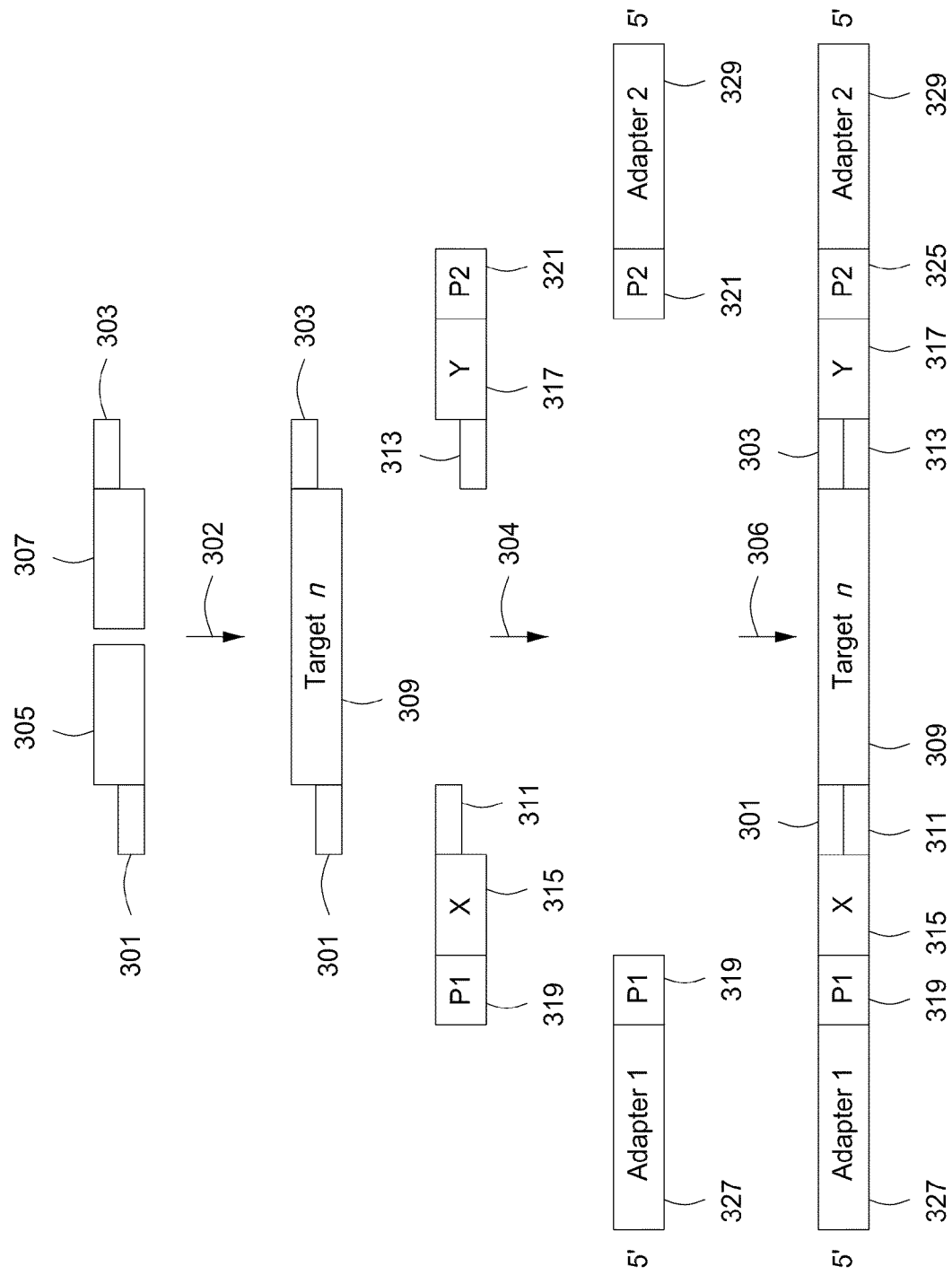
FIG. 3 is a representational depiction of one embodiment of the assay overviewed in FIG. 2.

In some particular embodiments, the assay system is used to analyze nucleic acids, e.g., by genotyping, quantitation of DNA copy number or RNA transcripts, localization of particular transcripts within samples, and the like. FIG. 3 illustrates an overall scheme for an exemplary assay for, e.g., detecting single nucleotide polymorphisms (SNPs) that can be used with the assay system of the invention. In FIG. 3, two oligonucleotide probes are provided. Each oligonucleotide probe comprises a target-specific region (located on either side of the SNP to be analyzed) seen at 305 and 307, and ligation regions, seen at 301 and 303. The oligonucleotide probes are allowed to hybridize to a target nucleic acid (not shown) in the biological sample. At step 302, one of the oligonucleotide probes is extended to incorporate the SNP sequence and ligated to the other probe to form an extended probe comprising target nucleic acid region 309 and ligation regions 301 and 303.

Two encoding agents, both comprising a coding tag (seen at 315 and 317), a ligation region (seen at 311 and 313), and a primer region (seen at 319 and 321) are combined with and ligated to the extended probe at step 304 to form an encoded target-specific oligonucleotide. Again, in contrast with FIG. 1, the probes and encoding agents are delivered at separate steps. Doing so allows use of the combinatorial embodiments described infra. In preferred embodiments, the encoding oligonucleotides within a pair of encoding oligonucleotides ligate specifically to one side of the target sequence or the other (i.e., 5' or 3' of the target sequence) in step 306. Also, typically, the ligation and primer regions of the encoding oligonucleotides and probes are universal; that is, the set of ligation and primer regions used in constructing the probes and encoding oligonucleotides are constant, and only the target-specific regions of the probes and the coding tags of the encoding oligonucleotides differ. However, again in alternative embodiments, the ligation and primer regions are not universal and differ between probes and encoding agents.

Following ligation, the encoded probes are eluted, pooled, and, optionally, sequencing adapters are added to the encoded probes via PCR. In alternative embodiments, sequencing primers may be ligated to the encoding oligonucleotides, or sequencing primer sequences can be included as part of the encoding oligonucleotide. As seen in FIG. 3, each sequencing adapter comprises primer region 319 or 321, compatible with the primer regions 319 and 321 on the encoded probes. The final construct comprising first adapter 327, first primer region 319, first coding tag 315, ligation regions 311 and 301, target region 309, ligation regions 313 and 303, second coding tag 317, second primer region 325 and second adapter 329 is now ready for input into a digital high-throughput sequencing process.

A combination of extension and ligation reactions are exemplified in FIG. 3, but it should be appreciated that a variety of reactions may be used to couple the encoding oligonucleotides to the target-specific oligonucleotides, including ligation only (e.g.,for oligonucleotides that hybridize to contiguous portions of the target nucleic acid sequence). Alternatively, an assay utilizing an additional oligonucleotide, such as in the GOLDENGATE® assay (see Fan, et al., Cold Spring Symp. Quant. Biol., 68:69-78 (2003); (Illumina, Inc., San Diego, Calif.)), may be employed.

In other embodiments, the assay system of the invention also can be used to analyze peptides or proteins, the presence of antibodies, enzymatic and other protein activities, post-translational modifications, active and non-active forms of peptides, as well as peptide isoforms in a biological sample.

Accordingly, the probes may comprise an active region of an enzyme, a binding domain of an immunoglobulin, defined domains of proteins, whole proteins, synthetic peptides, peptides with introduced mutations, aptamers and the like.

In certain aspects, the probes are substrates for enzymes or proenzymes, e.g., kinases, phosphatases, zymogens, proteases, or fragments thereof. In certain aspects, the probes are phosphorylation substrates used to detect proteins involved in one or more signal transduction pathways, e.g., a kinase or a phosphatase. In another specific aspect of the invention, the probes are specific protease substrates that associate only with individual proteases or classes of proteases. In other aspects, the probes are different processed forms, isoforms and/or domains of an enzyme. Protein-based probes are typically conjugated or otherwise linked to oligonucleotide encoding agents. The oligonucleotide encoding agents in this case would also include a nucleotide sequence component that allows for identification of the protein probe.

In certain aspects, the present invention provides assays for evaluating differences in the amount and/or activity of biological targets between different locations in a sample and/or between samples. The method includes determining a plurality of encoded results from the biological sample and evaluating the differences in quantity of the biological targets at each location in the biological sample.

Combinatorial Embodiments

To maximize the efficiency of encoding, a combinatorial approach using pairs of coding tags in the encoding oligonucleotides can be used. By de-coupling the target-specific information and the coding tags, the number of oligonucleotides required is dramatically reduced, with a concomitant decrease in cost.

Figure 4:
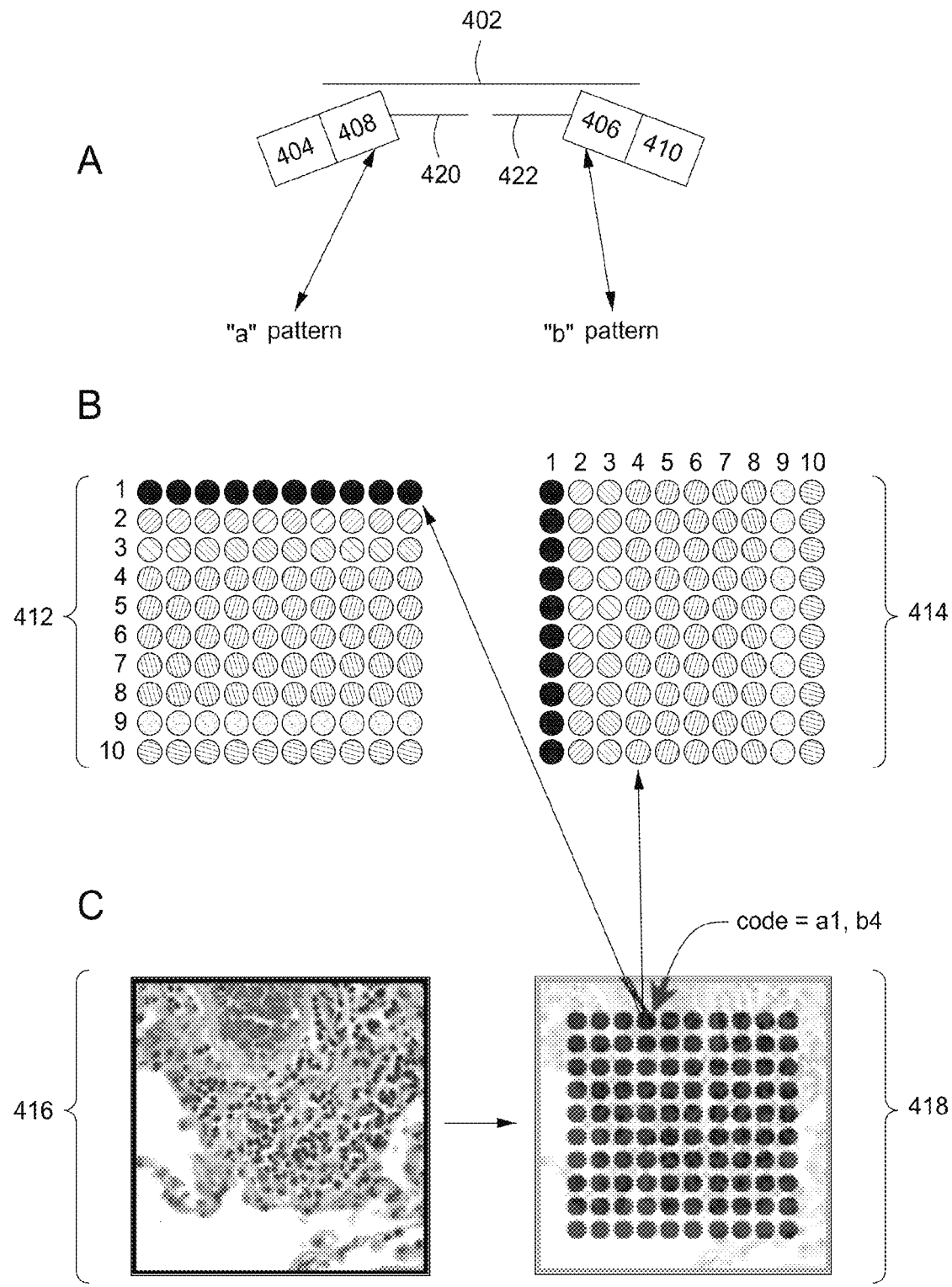
FIG. 4 illustrates a general mechanism for one embodiment of a combinatorial encoding scheme of the assay systems of the invention.

FIG. 4 illustrates a general mechanism for one embodiment of a combinatorial encoding scheme of the assay systems of the invention., where nucleic acids in a representative tissue section (shown at 416) are assayed. FIG. 4 at A shows two target-specific/encoding oligonucleotide constructs 420 and 422 (e.g., formed between steps 302 and 304 of FIG. 3) specifically bound to a target nucleic acid 402 of interest. The first encoded probe 420 comprises coding tag 408, associated with, e.g., a universal priming site for amplification of the assay products or an adapter to enable identification of the coding identifiers using sequencing technologies 404. The second encoded probe 422 comprises coding tag 406, associated with, e.g., a universal priming site for amplification of the assay products or an adapter to enable identification of the coding identifiers using sequencing technologies 410.

FIG. 4 at B shows the spatial pattern that may be used for twenty different coding tags, a1 through a10 (coding tag 406 on encoded probe 420) and b1 through b10 (coding tag 408 encoded probe 422). Coding tag a1, for example, is deposited on the biological sample in ten discrete areas or spots (shown as the first horizontal line of spots in 412). Coding tag a2 is deposited on the biological sample in ten spots on the second horizontal line in 412. Coding tag a3 is deposited on the biological sample in ten spots on the third horizontal line in 412, and so on. Whereas the "a" tags are deposited in ten horizontal rows, the "b" tags are deposited in ten vertical rows as shown in 414. For example, coding tag b1 is deposited on the biological sample in ten discrete spots in the first vertical row of 414, coding tag b2 is deposited on the biological sample in ten discrete spots in the second vertical row of 414, and so on. Using such a configuration allows for twenty coding tags to uniquely define 100 different locations on the biological sample.

FIG. 4 at C shows a representative tissue section 416 coincident with coding tag grid 418. The arrows show how the "a" coding tags and the "b" coding tags are deposited on grid 418 that is coincident with tissue section 416. If, once sequenced, coding tags a1 and b4, e.g., are associated with a target nucleic acid sequence, then that target nucleic acid sequence (i.e., biological target) was present in the tissue section at location a1, b4.

Figure 5:
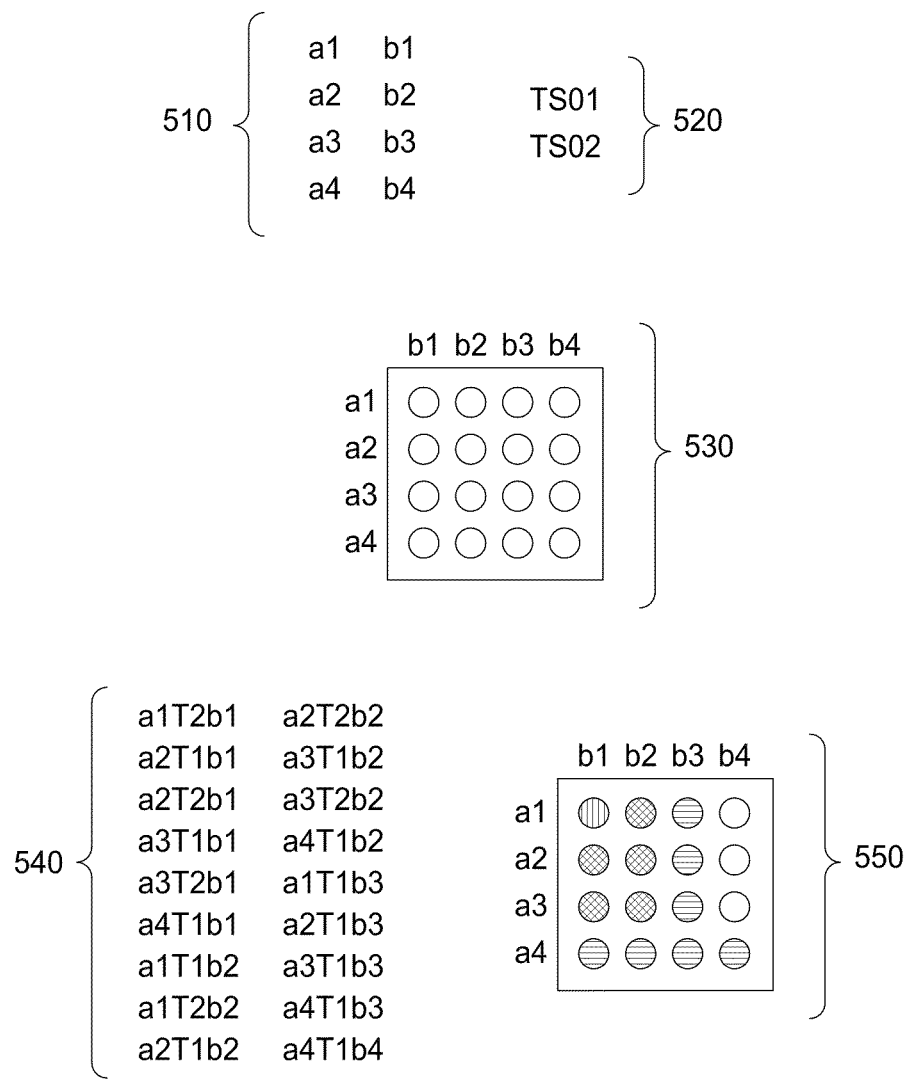
FIG. 5 provides a simplified, specific example of the embodiment of a combinatorial encoding scheme shown in FIG. 4.

FIG. 5 provides a simplified, specific example of the encoding scheme of the assay systems of the invention. FIG. 5 shows encoding oligonucleotides 510, comprising a1, a2, a3, a4 and b1, b3, b3 and b4. Target-specific oligonucleotides (TSOs) (probes) 1 and 2 are shown at 520. A deposit or dispensing scheme is shown at 530. Like the grid exemplified in FIG. 4, encoding oligonucleotides a1 through a4 are deposited in spots in a pattern (here, in a vertical pattern), and encoding oligonucleotides b1 through b4 are deposited in spots in a pattern (here, a horizontal pattern). The grid though shown as a square with spots is actually a deposition pattern on a biological sample (not shown) such as tissue section 416 shown in FIG. 4.

The target-specific oligonucleotides are delivered to the biological sample, where the target-specific oligonucleotides hybridize to target nucleic acids in the biological sample if target nucleic acids are present. Unhybridized target-specific oligonucleotides are then removed, e.g., by washing. The encoding oligonucleotides are then delivered to the biological sample according to the spatial pattern shown at 530. The encoding oligonucleotides are ligated (or, e.g., extended and ligated) to any target-specific oligonucleotides that hybridized to the target nucleic acid in the biological sample, the ligated constructs are then eluted from the biological sample, pooled, and sequencing adapters are added through, e.g., PCR or ligation, if the sequences were not previously included in the encoding oligonucleotides. The ligated constructs are sequenced by, e.g., high throughput or "next generation" sequencing.

The pool of resulting sequences is shown at 540. A sequence readout was obtained for target-specific oligonucleotide 1 only at a4b1, a4b2, a1b3, a2b3, a3b3, a4b3 and a4b4 (positions shown with horizontal lines). A sequence readout was obtained for target-specific oligonucleotide 2 only at a1b1 (position shown with vertical lines). A sequence readout was obtained for both target-specific oligonucleotides 1 and 2 at positions a2b1, a3b1, a1b2, a2b2, and a3b2 (positions shown with cross-hatching). No sequence readout was obtained for either target-specific oligonucleotides at a1b4, a2b4 or a3b4 (positions shown without shading). Thus, in the biological sample on which the assay took place the first target nucleic acid was detected in a large portion of the left side and at the bottom of the biological sample, the second target nucleic acid was detected only in the upper left portion of the biological sample, and neither target nucleic acid was detected in the upper right portion of the biological sample. The differential expression of the two target nucleic acids now can be mapped back to the biological sample and to the biological structures or cell types in these locations in the biological sample, as shown in 550.

In addition to location information, information relating to relative abundance of the encoded tags can be obtained. For example, if it is found that there are ten times as many a4T1b1 sequences occurring in the data set as compared to a4T1b2 sequences, this would indicate that target nucleic acid sequence 1 is ten times more abundant at the a4T1b1 location than at the a4T1b2 location.

In the case of nucleotide analysis as shown in FIG. 3, by ligating the coding tags directly to target-specific oligonucleotides, only 2n target-specific oligonucleotides are needed for n targets. For example, using the combinatorial approach outlined in FIG. 2, assaying 100 different targets at 10,000 spatial locations would require 2×100 target-specific oligonucleotides and 2×100 encoding oligonucleotides. The total count of assay oligonucleotides would be only 400 (200 target-specific and 200 encoding), not counting universal primers. In contrast, if the coding oligonucleotides were not decoupled from the target-specific oligonucleotides, (n×X positional codes)+(n×Y positional codes) would be needed, or in the above example, 20,000 oligonucleotides, not counting universal primer sequences. Moreover, though the embodiments shown in FIGS. 2-5 depict a combinatorial scheme using two encoding agents (coding tags), three, four or more encoding agents and coding tags may be used, and attached to the probe or one another by varying means and in varying combinations of steps.

Due to the spatial encoding aspect of the assay system of the invention, a large amount of information can be generated with even a modest number of assays. For example, five or more biological targets assayed at five or more positions in the sample generates 25 or more combinations. Using digital sequencing as a readout, the optimum number of sequence reads per combination depends on the sensitivity and dynamic range required, and can be adjusted. For example, if for each combination on average 100 reads are sampled, the total for 25 combination is 25,000 reads. If 1,000 targets are assayed at 1,000 locations with an average sampling depth of 1,000, then $10^9$ reads are required. These numbers, although large, are within the capacity of intrinsically parallel digital sequencing methods, which can generate datasets of billions or even trillions of reads in a reasonable timeframe and at a very low cost per read. Therefore, by varying the numbers of positions interrogated or biological targets assayed, or both, and using digital sequencing, large amounts of information can be obtained. In specific aspects, multiple locations are interrogated for two or more biological molecules.

Reagent Delivery Systems

The reagent delivery system of the invention includes instrumentation that allows the delivery of reagents to discrete portions of the biological sample, maintaining the integrity of the spatial patterns of the encoding scheme. Reagent delivery systems of the assay systems of the invention comprise optional imaging means, reagent delivery hardware and control software. Reagent delivery can be achieved in a number of different ways. It should be noted that reagent delivery may be to many different biological samples at one time. A single tissue section has been exemplified herein; however, multiple biological samples may be affixed and analyzed simultaneously. For example, serial sections of a tissue sample can be analyzed in parallel and the data combined to build a 3D map.

Integral to the assay system of the invention is instrumentation that allows for spatial patterning of reagents onto the biological sample. Technologies for formulating and delivering both biological molecules (e.g. oligonucleotides or antibodies) and chemical reagents (e.g., small molecules or dNTPs) are known in the art, and uses of these instrument systems are known to one skilled in the art and easily adaptable to the assay systems of the invention. One example of a suitable reagent delivery system is the Labcyte™ Echo acoustic liquid handler, which can be used to deliver nanoliter scale droplets containing biological molecules with high precision and reproducibility. One skilled in the art could incorporate this reagent delivery device into the overall system, using software to specify the locations to which reagents should be delivered.

Other instruments that can be used for the deposition of agents and/or coding identifiers onto biological samples include, but are not limited to, ink jet spotting; mechanical spotting by means of pin, pen or capillary; micro contact printing; photochemical or photolithographic methods; and the like. For several applications, it may be preferred to segment or sequester certain areas of the biological samples into one or more assay areas for different reagent distributions and/or biological target determination. The assay areas may be physically separated using barriers or channels.

In one exemplary aspect, the reagent delivery system may be a flow-based system. The flow-based systems for reagent delivery in the present invention can include instrumentation such as one or more pumps, valves, fluid reservoirs, channels, and/or reagent storage cells. Reagent delivery systems are configured to move fluid to contact a discrete section of the biological sample. Movement of the reagents can be driven by a pump disposed, for example, downstream of the fluid reagents. The pump can drive each fluid reagent to (and past) the reaction compartment. Alternatively, reagents may be driven through the fluid by gravity. US Pub. Nos. 20070166725 and 20050239192 disclose certain general-purpose fluidics tools that can be used with the assay systems of the invention, allowing for the precise manipulation of gases, liquids and solids to accomplish very complex analytical manipulations with relatively simple hardware.

In a more specific example, one or more flow-cells can be attached to the substrate-affixed biological sample from above. The flow-cell can include inlet and outlet tubes connected thereto and optionally an external pump is used to deliver reagents to the flow-cell and across the biological sample. The flow cells are configured to deliver reagents only to certain portions of the biological sample, restricting the amount and type of reagent delivered to any specific section of the biological sample.

In another aspect, a microfluidic system can be integrated into the substrate upon which the biological sample is disposed or externally attached on top of the substrate. Microfluidic passages for holding and carrying fluid may be formed on and/or above the planar substrate by a fluidics layer abutted to the substrate. Fluid reagents can be selected and delivered according to selective opening and closing of valves disposed between reagent reservoirs.

Pumps generally include any mechanism for moving fluid and/or reagents disposed in fluid. In some examples, the pump can be configured to move fluid and/or reagents through passages with small volumes (i.e., microfluidic structures). The pump can operate mechanically by exerting a positive or negative pressure on fluid and/or on a structure carrying fluid, electrically by appropriate application of an electric field(s), or both, among other means. Exemplary mechanical pumps may include syringe pumps, peristaltic pumps, rotary pumps, pressurized gas, pipettors, etc. Mechanical pumps may be micromachined, molded, etc. Exemplary electrical pumps may include electrodes and may operate by electrophoresis, electroendoosmosis, electrocapillarity, dielectrophoresis (including traveling wave forms thereof), and/or the like.

Valves generally include any mechanism for regulating the passage of fluid through a channel. Valves can include, for example, deformable members that can be selectively deformed to partially or completely close a channel, a movable projection that can be selectively extended into a channel to partially or completely block a channel, an electrocapillary structure, and/or the like.

An open gasket can be attached to the top of the biological sample and the sample and reagents can be injected into the gasket. Suitable gasket materials include, but are not limited to, neoprene, nitrile, and silicone rubber. Alternatively, a watertight reaction chamber may be formed by a gasket sandwiched between the biological sample on the substrate and a chemically inert, water resistant material such as, but not limited to, black-anodized aluminum, thermoplastics (e.g., polystyrene, polycarbonate, etc), glass, etc.

In an optional embodiment, the assay system comprises imaging means to determine features and organization of the biological sample of interest. The images obtained, e.g., may be used to design the deposition pattern of the reagents. Imaging means are optional, as an individual can instead view the biological sample using, e.g., a microscope, analyze the organization of the biological sample, and specify a spatial pattern for delivery assay reagents. If included, the delivery system can comprise a microcircuit arrangement including an imager, such as a CCD or IGFET-based (e.g., CMOS-based) imager and an ultrasonic sprayer for reagent delivery such as described in US Pub. No. 20090197326, which is incorporated herein by reference. Also, it should be noted that although FIGS. 4 and 5 illustrate using a x,y grid configuration, other configurations can be used, such as, e.g., following the topology of a tissue sample; targeting certain groups of cells, cell layers and/or cell types in a tissue, and the like.

In yet another alternative, the reagent delivery system controls the delivery of reagents to specific patterns on a biological sample surface using semiconductor techniques such as masking and spraying. Specific areas of a biological sample can be protected from exposure to reagents through use of a mask to protect specific areas from exposure. The reagents may be introduced to the biological sample using conventional techniques such as spraying or fluid flow. The use of masked delivery results in a patterned delivery scheme on the substrate surface.

In a preferred aspect of the invention, the reagent delivery instrumentation is based on inkjet printing technology. There are a variety of different ink jetting mechanisms (e.g., thermal, piezoelectric) and compatibility has been shown with aqueous and organic ink formulations. Sets of independently actuated nozzles can be used to deliver multiple reagents at the same time, and very high resolutions are be achieved.

In order to target specific sites of interest, an informative image of the biological sample to be assayed may be used to assist in the reagent delivery methods and associated encoding scheme. Sample regions of the biological sample can be identified using image processing (e.g., images of cell types differentiated by immunohistochemistry or other staining chemistries) integrated with other features of the assay system. In some aspects, software is used to automatically translate image information into a reagent delivery pattern. A mechanism to register and align very precisely the biological sample for reagent delivery is thus an important component of the assay systems of the invention. Mechanisms such as the use of fiducial markers on slides and/or other very accurate physical positioning systems can be adapted to this purpose.

The invention preferably comprises a complete suite of software tailored to the assay system. Optionally, oligonucleotide design software is used to design the encoding nucleotides (and in embodiments where nucleic acids are assayed, the target-specific oligonucleotides) for the specific assay to be run, and may be integrated as a part of the system. Also optionally, algorithms and software for reagent delivery and data analysis (i.e.,sequence analysis) may be integrated to determine assay results. Integrated data analysis is particularly useful, as the type of dataset that is generated may be massive as a consequence of scale. Algorithms and software tools that are specifically designed for analysis of the spatially-associated data generated by the assay systems, including pattern-analysis software and visualization tools, enhance the value of the data generated by the assay systems.

In certain aspects, the assay system comprises processes for making and carrying out the quality control of reagents, e.g., the integrity and sequence fidelity of oligonucleotide pools. In particular, reagents are formulated according to factors such as volatility, stability at key temperatures, and chemical compatibility for compatibility with the reagent delivery instrumentation and may be analyzed by instrumentation integrated within the assay system.

Sequencing

Numerous methods can be used to identify the coding tags and probe sequences in the encoded probes of the assay systems of the invention. The coding tags can be detected using techniques such as mass spectroscopy (e.g., Maldi-T of, LC-MS/MS), nuclear magnetic resonance imaging, or, preferably, nucleic acid sequencing. Examples of techniques for decoding the coding tags of the present invention can be found, for example, in US Pub. No. 20080220434, which is incorporated herein by reference. For example, the coding tags may be oligonucleotide mass tags (OMTs or massTags). Such tags are described, e.g., in US Pub. No. 20090305237, which is incorporated by reference in its entirety. In yet another alternative, the encoded probes can be amplified and hybridized to a microarray. This would require separate amplification reactions to be carried out, in which each amplification is specific to a particular spatial code or subset of codes, accomplished by using code-specific primers. Each amplification would also incorporate a different resolvable label (e.g. fluorophor). Following hybridization, the relative amounts of a particular target mapping to different spatial locations in the sample can be determined by the relative abundances of the resolvable labels.

In one particularly preferred aspect, the resulting coding tags according to the assay system are substrates for high-throughput, next-generation sequencing, and highly parallel next-generation sequencing methods are used to confirm the sequence of the coding tags, for example, with SOLiD™ technology (Life Technologies, Inc.) or Genome Ananlyzer (Illumina, Inc.). Such next-generation sequencing methods can be carried out, for example, using a one pass sequencing method or using paired-end sequencing. Next generation sequencing methods include, but are not limited to, hybridization-based methods, such as disclosed in e.g., Drmanac, U.S. Pat. Nos. 6,864,052; 6,309,824; and 6,401,267; and Drmanac et al, U.S. patent publication 2005/0191656; sequencing-by-synthesis methods, e.g., U.S. Pat. Nos. 6,210, 891; 6,828,100; 6,969,488; 6,897,023; 6,833,246; 6,911,345; 6,787,308; 7,297,518; 7,462,449 and 7,501,245; US Publication Application Nos. 20110059436; 20040106110; 20030064398; and 20030022207; Ronaghi, et al, Science, 281:363-365 (1998); and Li, et al, Proc. Natl. Acad. Sci., 100:414-419 (2003); ligation-based methods, e.g., U.S. Pat. Nos. 5,912,148 and 6,130,073; and U.S. Pat. Appln Nos. 20100105052, 20070207482 and 20090018024; nanopore sequencing e.g., U.S. Pat. Appln Nos. 20070036511; 20080032301; 20080128627; 20090082212; and Soni and Meller, Clin Chem 53:1996-2001 (2007)), as well as other methods, e.g., U.S. Pat. Appln Nos. 20110033854; 20090264299; 20090155781; and 20090005252; also, see, McKernan, et al., Genome Res., 19:1527-41 (2009) and Bentley, et al., Nature 456:53-59 (2008), all of which are incorporated herein in their entirety for all purposes.

Applications of Assay System

It will be apparent to one skilled in the art upon reading the present disclosure that there are numerous important areas of biological research, diagnostics, and drug development that will benefit from a high throughput multiplexed assay system that can measure simultaneously the amount and spatial location of a biological target in a biological sample. For example, combining the ability to estimate the relative abundance of different RNA trancripts with the ability to reconstruct an image of spatial patterns of abundance across many locations, which may be as small as or even smaller than individual cells, in a tissue enables many different areas of basic research. The following are exemplary uses and are by no means meant to be limiting in scope.

In one example, 3-dimensional patterns of gene expression are determined by analyzing a series of tissue sections, in a manner analogous to image reconstruction in CT scanning Such a method can be used to measure changes in gene expression in disease pathology, e.g., in cancerous tissue and/or a tissue upon injury, inflammation or infection. With the assay systems of the invention, more detailed information on gene expression and protein localization in complex tissues is obtained, leading to new insights into the function and regulation both in normal and diseased states, and provides new hypotheses that can be tested. For example, an assay system of the invention may enable some of the insights gained from many individual studies and larger programs like ENCODE (Birney, et al., Nature, 447:799-816 (2007)) and modENCODE to be integrated at the tissue level. The assay systems also aid computational efforts to model interacting networks of gene expression in the field of systems biology.

The assay systems also provide a novel approach to analysis of somatic variation, e.g., somatic mutations in cancer or variability in response to infectious organisms. For example, tumors are typically highly heterogeneous, containing cancer cells as well as genetically normal cells in an abnormal local environment. Cancer cells undergo mutation and selection, and in this process it is not unusual for local clones to develop. Identifying relatively rare somatic mutations in the context of tumors may enable the study of the role of key mutations in the selection of clonal variants. Transcriptional patterns associated with angiogenesis, inflammation, or other cancer-related processes in both cancer and genetically normal cells can be analyzed for insights into cancer biology and assist in the development of new therapeutic agents for the treatment of cancers. In another example, individuals have varying susceptibility to infectious organisms, and the assay systems of the invention can be used to study the interaction between microbes and tissues or the various cell types within the tissue.

Importantly, in addition to providing spatially-associated information, the invention allows a great increase in the sensitivity of detecting rare mutations, as signal to noise can be dramatically increased since only a small location is assayed in any given reaction. In a typical assay for rare mutations in a mixed sample, the sample is treated in bulk, i.e., nucleic acids are extracted from many cells into a single pool. Thus, if a mutation is present in one cell in 10,000, it must be detected against a background of normal DNA from ~10,000 cells. In contrast, with the assay systems of the invention many cells can be analyzed, but individual cells or small groups of cells would be identified by the spatial coding system. Therefore, in the assay systems of the present invention, background is reduced by orders of magnitude, greatly increasing sensitivity. Furthermore, the spatial organization of mutant cells can be observed, which may be particularly important in detecting key mutations in tissue sections in cancer. Already molecular histological analyses are yielding insights into cancer biology and may have potential for use in diagnostics. The technology of the invention promises to greatly increase the power of such approaches.

EXAMPLES

The following examples are put forth so as to provide those of ordinary skill in the art with a complete disclosure and description of how to make and use the present invention, and are not intended to limit the scope of what the inventor regards as his invention, nor are they intended to represent or imply that the experiments below are all of or the only experiments performed. It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees centigrade, and pressure is at or near atmospheric.

Example 1

Initial Proof of Concept of Encoding Scheme

As an initial proof of concept, a model system is developed using a microarray to demonstrate a working single-plex assay. The basic design validates the concept of the assay, and establishes a working assay prior to addressing issues related to the analysis of a more complicated biological sample. Conventional sequencing is used as a readout for this proof of concept.

A microarray is used as a proxy for a tissue section. The target sequences of the microarray are fully specified, so that the composition of the targets are known and can be varied systematically. Synthetic oligonucleotide templates are attached to a glass slide via a 5' amino modification. Each slide has a single oligonucleotide template sequence, and the assays that are carried out may employ either ligation, or extension followed by ligation as this may be useful in determining certain polymorphisms.

Once the in situ part of the assay is complete, the reaction products are eluted and analyzed by qPCR to determine presence or absence of a product and estimate yield, and by conventional sequencing to determine the structure of the assay products. The single-plex assays that are tested include appropriate positive and negative controls, and a single nucleotide variant (SNV) to check ability to discriminate single base variants.

Example 2

Scalability

The complexity of the assay system is increased to establish scalability of the assay for use in high throughput studies. Scalability of both the spatial encoding and assay systems is demonstrated by carrying out a 24-plex×24-site assay using a microarray model system.

The amount of biological target, here a DNA target sequence, at each assay location is systematically varied on microarray substrate. For example, in a microarray with 50 micron spot size (center to center), a 1 $mm^2$ area contains ~400 spots. The region around each site is optionally occupied by a region that is devoid of these spots to allow individual resolvability of the target sequences. Alternatively, the spots may be clustered, with two or more directly adjacent spots surrounded by or adjacent to a region that is devoid of target sequences.

In order to demonstrate that spatial encoding is accurate, the sites comprise different target compositions to show that the assay readout matches the expected composition of each site. With 24 target sequences, a simple digital pattern is made with each site having a different set of 12 targets present and 12 targets absent, to make a binary code (0=absent, 1=present). The assay readout is then determined to show that the detected regions match the expected signal after spatial decoding. In this particular example, the code space is large enough ($2^{24}$) so that even a few errors would not result in different codes being mixed up. Moreover, this design allows identification of errors and allows an estimation not only of accuracy of spatial encoding but also of accuracy calling the presence or absence of target sequences.

The ability to detect quantitative differences is evaluated by generating dose-response curves for each of the 24 assays that are carried out at each site in a 24-site assay. This allows estimation of the limit of detection, dynamic range, and power to detect a given fold-change across the range.

In one aspect, a latin square design is used to represent individual targets at different ratios by varying the number of features for each target. In other words, with multiple spots in a site, the number of spots allocated to each of the 24 target sequences can be varied and each of the 24 sites can have a different composition. A 1×3 inch microarray is sufficiently large to permit multiple replicates. This larger set of 24 sequences will require deconvolution, and this is accomplished using high throughput techniques such as next-generation sequencing technologies (e.g., SOLiD™ technology (Life Technologies, Inc., Carlsbad, Calif.) or Genome Analyzer (Illumina, Inc., San Diego, Calif.)). The use of the 24-plex assay demonstrates both the accuracy of spatial encoding and decoding, and the quantitative response of the assay system.

Example 3

Adaptation of the Assay to Preserved Samples

Genomic DNA is assayed as a proof of concept for assaying RNA, as it provides a way to establish a single-copy reference signal. Once a working assay is developed for FFPE samples, it is adapted to an RNA assay. To this end, assay oligonucleotide concentrations are assayed to ensure compatibility with high multiplexing. Assuming a cell diameter of 10 microns, and delivery of a 10 micron diameter reagent droplet to an individual cell, the volume of the droplet will be ~500 µl and can contain ~$3\times10^{11}$ molecules at a 1 µM concentration. To assay 1,000 target sequences in 10,000 cells, ~2,000 targeting oligonucleotides would be required in a droplet. Therefore, each droplet could contain ~160 million copies of each assay oligo, a vast excess over the few thousand target sequences in a cell.

The handling of small absolute numbers of product molecules generated from very small or compromised samples are enhanced to counter the issue of low recovery efficiency; that is, elution is efficient and losses resulting from adsorption of molecules to surfaces are prevented. An approach to addressing the latter issue is to include a carrier material, such as glycogen or carrier nucleic acids.

Example 4

Adapting the Assay to a Biological Sample

A control RNA template is immobilized to a solid support in order to create an artificial system. The assay is performed using T4 DNA ligase, which can repair nicks in DNA/RNA hybrids. Assays are carried out on matched slides, or different sections of the same slide, where in one case gDNA is assayed and in the other RNA is assayed. When assaying gDNA the slide can be pretreated with RNase, and when assaying RNA the slide is pretreated with DNase. Results of the assay are confirmed by extracting gDNA or RNA and quantitating the relative amounts by qPCR or RT-qPCR respectively.

In order make the tissue section RNA assays as informative as possible, pre-existing information on expression levels in specific tissues to target transcripts across a range of abundances are used in the assay design. Both high abundance transcripts, as well as some medium and low abundance transcripts, are targeted to enable an initial assessment of the quantitative performance characteristics of the assay.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims. In the claims that follow, unless the term "means" is used, none of the features or elements recited therein should be construed as means-plus-function limitations pursuant to 35 U.S.C. §112, ¶6.

I claim:

1. A method to determine the abundance or activity or both of a biological target in a sample, comprising the following steps:
   delivering encoded probes for a biological target to multiple sites in a sample affixed to a support, wherein each encoded probe comprises a probe region capable of specific binding to the biological target and a coding tag comprising an oligonucleotide that identifies the location of the site to which the encoded probe is delivered;
   allowing the encoded probes to interact with the biological target;
   separating encoded probes specifically bound to the biological target from encoded probes not specifically bound to the biological target;
   pooling encoded probes specifically bound to the biological target;
   determining all or a portion of the coding tag oligonucleotide sequence of the encoded probe in the pool by performing a polynucleotide sequencing reaction of the encoded probe, thereby identifying the location of the site to which the encoded probe is delivered; and
   associating the abundance or activity or both of the biological target to the locations of the multiple sites in the sample.

2. The method of claim 1, wherein the biological target is a nucleic acid and the encoded probes are oligonucleotides.

3. The method of claim 2, wherein there are two encoded probes for the nucleic acid target at each of the multiple sites in the sample.

4. The method of claim 1, wherein the biological target is a protein, the probe regions of the encoded probes are proteins, and the coding tags comprise oligonucleotides.

5. The method of claim 4, wherein the biological target comprises an enzyme.

6. The method of claim 1, wherein each of the probe regions of the encoded probes comprises an antibody, an aptamer, and/or a small molecule that is capable of specific binding to the biological target.

7. The method of claim 1, further comprising an amplification step between the separating step and the determining step.

8. The method of claim 1, wherein the determining step is performed by nucleic acid sequencing or high-throughput sequencing or high-throughput digital nucleic acid sequencing.

9. The method of claim 1, wherein multiple biological targets in the sample are assayed and the product of the multiple biological targets being assayed and the multiple sites in the sample is greater than 20, 50, 75, 100, 1,000, 10,000, 100,000, or 1,000,000.

10. The method of claim 1, wherein the sequences of at least one hundred thousand, at least five hundred thousand, or at least one million encoded probes are determined in parallel.

11. The method of claim 1, wherein software programmed hardware performs at least two steps of the delivering step, the separation step, the determining step and the associating step.

12. The method of claim 1, wherein the probe regions of the encoded probes are proteins and the separating step is accomplished by capturing encoded probes specifically bound to the biological target using an affinity capture agent.

13. The method of claim 1, wherein the probe regions of the encoded probes are nucleic acids and the separating step is accomplished by washing the sample.

14. The method of claim 1, wherein in the associating step, the abundance or activity or both of the biological target is associated to the locations of the multiple sites in the sample to determine a spatial pattern of abundance or activity or both of the biological target in the sample.

15. A method to determine the abundance or activity or both of a nucleic acid target in a sample, comprising the following steps:
   delivering an oligonucleotide probe capable of specific hybridization with a nucleic acid target to multiple sites in a sample affixed to a support;
   allowing the oligonucleotide probe to hybridize with the nucleic acid target;
   washing unhybridized oligonucleotide probe from the sample;
   delivering one or more encoding agents to the multiple sites in the sample, wherein the one or more encoding agents delivered to each site comprise an oligonucleotide that identifies the location of the site in the sample;
   coupling the one or more encoding agents and the oligonucleotide probe delivered to each site to form an encoded probe specifically hybridized with the nucleic acid target at the site;
   pooling encoded probes specifically hybridized with the nucleic acid target;
   determining all or a portion of the one or more encoding agent oligonucleotide sequences of the encoded probe in the pool by performing a polynucleotide sequencing reaction of the encoded probe, thereby identifying the location of the site to which the one or more encoding agents are delivered; and
   associating the abundance or activity or both of nucleic acid target to the locations of the multiple sites in the sample.

16. The method of claim 15, wherein multiple nucleic acid targets in the sample are assayed and the product of the multiple nucleic acid targets being assayed and the multiple sites in the sample is greater than 20, 50, 75, 10,000, 100,000, or 1,000,000.

17. The method of claim 15, wherein the sequences of at least one hundred thousand or at least one million encoded probes are determined in parallel.

18. The method of claim 15, wherein two oligonucleotide probes are delivered for the nucleic acid target.

19. The method of claim 15, wherein the coupling step is performed by ligation.

20. The method of claim 15, wherein the coupling step is performed by extension followed by ligation.

21. The method of claim 15, further comprising an amplification step between the coupling step and the determining step.

22. The method of claim 15, wherein in the associating step, the abundance or activity or both of the nucleic acid target is associated to the locations of the multiple sites in the sample to determine a spatial pattern of abundance or activity or both of the nucleic acid target in the sample.

23. A method of determining the abundance or activity or both of a biological target in a sample, comprising:
   delivering a probe capable of specific binding to a biological target to multiple sites in a sample affixed to a support;
   allowing the probe to interact with the biological target at each of the multiple sites in the sample;
   delivering an encoding agent to each of the multiple sites in the sample, wherein the encoding agent delivered to each site comprises an oligonucleotide that identifies the location of the site in the sample;
   coupling the encoding agent to the probe delivered to each of the multiple sites to form an encoded probe at each of the multiple sites;
   pooling encoded probes specifically bound to the biological target;
   determining all or a portion of the encoding agent oligonucleotide sequence of the encoded probe in the pool by performing a polynucleotide sequencing reaction of the encoded probe, thereby identifying the location of the site to which the encoding agent is delivered; and
   associating the abundance or activity or both of the biological target at each of the multiple sites to the locations of the multiple sites in the sample.

24. The method of claim 23, wherein one or more biological targets in the sample are assayed in parallel.

25. The method of claim 24, wherein for each biological target, one or more probes capable of specific binding to the biological target are delivered to the multiple sites in the sample.

26. The method of claim 23, wherein at least two encoding agents are delivered to each of the multiple sites in the sample and are coupled to the probe delivered to the site to form an encoded probe comprising the at least two encoding agents.

27. The method of claim 23, wherein the biological target comprises a nucleic acid and the probe comprises an oligonucleotide.

28. The method of claim 23, wherein the biological target comprises a protein and the probe comprises a protein.

29. The method of claim 23, wherein the biological target comprises an enzyme, and the probe comprises a substrate or putative substrate for the enzyme.

30. The method of claim 23, wherein the probe comprises an affinity capture agent, antibody, aptamer, or small molecule.

31. The method of claim 23, further comprising amplifying all or a portion of a sequence of the encoded probe.

32. The method of claim 23, wherein the determining step is performed by nucleic acid sequencing or high-throughput sequencing.

33. The method of claim 23, wherein multiple biological targets in the sample are assayed and the product of the multiple biological targets being assayed and the multiple sites in the sample is greater than 20, 50, 75, 100, 1,000, 10,000, 100,000, or 1,000,000.

34. The method of claim 23, wherein the sequences of at least one hundred thousand, at least five hundred thousand, or at least one million encoded probes are determined in parallel.

35. The method of claim 23, wherein the probe for the biological target and/or the encoding agent are delivered to the multiple sites in the sample according to a known spatial pattern.

36. The method of claim 23, wherein software programmed hardware performs at least two steps of the delivering steps, the coupling step, the determining step, and the associating step.

37. The method of claim 23, further comprising separating probes specifically bound to the biological target from probes not specifically bound to the biological target.

38. The method of claim 37, wherein the separating step is accomplished by washing the sample.

39. The method of claim 23, wherein the coupling step is performed by ligation, or performed by extension followed by ligation.

40. The method of claim 23, wherein the biological target is a nucleic acid and the probe is capable of specific hybridization with the nucleic acid target, wherein the probe sequence identifies the nucleic acid target.

41. The method of claim 40, wherein in the determining step, the encoded probe sequence being determined comprises all or a portion of the probe sequence and all or a portion of the encoding agent oligonucleotide sequence.

42. The method of claim 41, further comprising quantification of the encoded probe sequence being determined, wherein:
    the determined probe sequence identifies the nucleic acid target;
    the determined encoding agent oligonucleotide sequence identifies the location of the site at which the probe specific hybridizes with the nucleic acid target; and
    the quantity of the encoded probe sequence indicates the amount of the probe specifically hybridized with the nucleic acid target at the site in the sample, and thereby indicates the abundance or activity of the nucleic acid target at the site in the sample.

43. The method of claim 23, wherein the biological target is a protein, the probe is capable of specific binding to the protein target and comprises an oligonucleotide sequence that identifies the protein target.

44. The method of claim 43, wherein in the determining step, the encoded probe sequence being determined comprises all or a portion of the probe oligonucleotide sequence and all or a portion of the encoding agent oligonucleotide sequence.

45. The method of claim 44, further comprising quantification of the encoded probe sequence being determined, wherein:
    the determined probe oligonucleotide sequence identifies the protein target;
    the determined encoding agent oligonucleotide sequence identifies the location of the site at which the probe specific binds to the protein target; and
    the quantity of the encoded probe sequence indicates the amount of the probe specifically binds to the protein target at the site in the sample, and thereby indicates the abundance or activity of the protein target at the site in the sample.

46. The method of claim 23, wherein in the associating step, the abundance or activity or both of the biological target is associated to the locations of the multiple sites in the sample to determine a spatial pattern of abundance or activity or both of the biological target in the sample.

* * * * *